(12) United States Patent
Jimenez et al.

(10) Patent No.: US 7,855,214 B2
(45) Date of Patent: Dec. 21, 2010

(54) FUSED CYCLIC SYSTEMS USEFUL AS INHIBITORS OF TEC FAMILY PROTEIN KINASES

(75) Inventors: Juan-Miguel Jimenez, Abingdon (GB); Sanjay Patel, Abingdon (GB); David Kay, Abingdon (GB); Ronald Knegtel, Abingdon (GB); Oliver Philps, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 836 days.

(21) Appl. No.: 11/046,664

(22) Filed: Jan. 26, 2005

(65) Prior Publication Data
US 2005/0209255 A1 Sep. 22, 2005

Related U.S. Application Data
(60) Provisional application No. 60/539,176, filed on Jan. 26, 2004.

(51) Int. Cl.
*C07D 487/22* (2006.01)
*C07D 487/14* (2006.01)
*A61K 31/519* (2006.01)
*A61P 35/00* (2006.01)
*A61P 29/00* (2006.01)

(52) U.S. Cl. .................. 514/257; 544/247; 544/250; 514/267

(58) Field of Classification Search .............. 514/228.8, 514/242, 252.05, 252.16, 267, 259.1, 257; 544/279, 182, 238, 112, 117, 247, 250
See application file for complete search history.

(56) References Cited

U.S. PATENT DOCUMENTS
4,455,312 A 6/1984 Portnyagina et al.

FOREIGN PATENT DOCUMENTS
| | | | |
|---|---|---|---|
| GB | 2125785 | | 3/1984 |
| SU | 1174433 | A1 * | 8/1985 |
| SU | 1268170 | A  * | 11/1986 |
| SU | 1323560 | A1 * | 7/1987 |
| WO | 03077921 | | 9/2003 |

OTHER PUBLICATIONS
International Search Report for corresponding PCT Application No. PCT/US2005/002725, Jun. 28, 2005.
Database Registry, American Chemical Society; Feb. 28, 2003, XP002331999.
Database Registry, American Chemical Society; Jan. 21, 2003, XP002332000.
Database Chemical Abstracts, STN Database Accession No. XP002332001, 1963.
Orfi et al. "Heterocondensed Quinazolones: Synthesis and protein-tyrosine kinase inhibitory activity of 3,4-dihydro-1H, 6H-[1,4]oxazino-[3,4-b]quinazolin-6-one derivatives", Bioorganic and Medicinal Chemistry, 4(4), 547-551, (1996).
Parfitt et al, "Cyclic amidines. XVI. Tetraazanaphtho[1,2,3-fg]naphthacenes" J. Chem. Soc. (1963) pp. 3062-3066.

* cited by examiner

*Primary Examiner*—James O Wilson
*Assistant Examiner*—Cecilia M Jaisle
(74) *Attorney, Agent, or Firm*—Jennifer G. Che

(57) ABSTRACT

The present invention relates to compounds useful as inhibitors of Tec family protein kinases. These compounds have the general formula I:

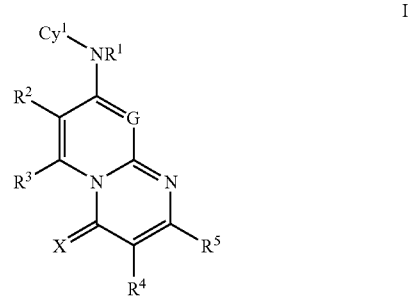

or a pharmaceutically acceptable salt thereof, wherein $R^1$, $R^2$, $R^3$, $R^4$, $R^5$, G, $Cy^1$, and X are as defined herein. The invention also provides pharmaceutically acceptable compositions comprising said compounds and methods of using the compositions in the treatment of various disease, conditions, or disorders.

36 Claims, No Drawings

FUSED CYCLIC SYSTEMS USEFUL AS INHIBITORS OF TEC FAMILY PROTEIN KINASES

CROSS-REFERENCE TO RELATED APPLICATION(S)

This application claims the benefit under 35 U.S.C. §119 of U.S. Provisional Application 60/539,176, filed Jan. 26, 2004, the entire contents of the provisional application being incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Tec family of non-receptor tyrosine kinases plays a central role in signalling through antigen-receptors such as the TCR, BCR and Fcε receptors (reviewed in Miller A, et al. Current Opinion in Immunology 14;331-340 (2002). Tec family kinases are essential for T cell activation. Three members of the Tec family, Itk, Rlk and Tec, are activated downstream of antigen receptor engagement in T cells and transmit signals to downstream effectors, including PLC-γ. Deletion of Itk in mice results in reduced T cell receptor (TCR)-induced proliferation and secretion of the cytokines IL-2, IL-4, IL-5, IL-10 and IFN-γ (Schaeffer et al, Science 284; 638-641 (1999)), Fowell et al, Immunity 11;399-409 (1999), Schaeffer et al Nature Immunology 2,12; 1183-1188 (2001))). The immunological symptoms of allergic asthma are attenuated in Itk−/− mice. Lung inflammation, eosinophil infiltration and mucous production are drastically reduced in Itk−/− mice in response to challenge with the allergen OVA (Mueller et al, Journal of Immunology 170: 5056-5063 (2003)). Itk has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International archives of Allergy and Immunology 129; 327-340 (2002)).

Splenocytes from Rlk−/− mice secrete half the IL-2 produced by wild type animals in response to TCR engagement (Schaeffer et al, Science 284; 638-641 (1999)), while combined deletion of Itk and Rlk in mice leads to a profound inhibition of TCR-induced responses including proliferation and production of the cytokines IL-2, IL-4, IL-5 and IFN-γ (Schaeffer et al Nature Immunology 2,12; 1183-1188 (2001)), Schaeffer et al, Science 284; 638-641 (1999)). Intracellular signalling following TCR engagement is effected in Itk/Rlk deficient T cells; inositol triphosphate production, calcium mobilization, MAP kinase activation, and activation of the transcription factors NFAT and AP-1 are all reduced (Schaeffer et al, Science 284; 638-641 (1999), Schaeffer et al Nature Immunology 2,12; 1183-1188 (2001)).

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5:d917-928). Mice deficient in Btk also have a reduced number of peripheral B cells and greatly decreased levels of IgM and IgG3. Btk deletion in mice has a profound effect on B cell proliferation induced by anti-IgM, and inhibits immune responses to thymus-independent type II antigens (Ellmeier et al, J Exp Med 192:1611-1623 (2000)).

Tec kinases also play a role in mast cell activation through the high-affinity IgE receptor (FcεRI). Itk and Btk are expressed in mast cells and are activated by FcεRI cross-linking (Kawakami et al, Journal of Immunology; 3556-3562 (1995)). Btk deficient murine mast cells have reduced degranulation and decreased production of proinflammatory cytokines following FcεRI cross-linking (Kawakami et al. Journal of leukocyte biology 65:286-290). Btk deficiency also results in a decrease of macrophage effector functions (Mukhopadhyay et al, Journal of Immunology; 168, 2914-2921 (2002)).

Accordingly, there is a great need to develop compounds useful as inhibitors of protein kinases. In particular, it would be desirable to develop compounds that are useful as inhibitors of Tec family (e.g., Tec, Btk, Itk/Emt/Tsk, Bmx, Txk/Rlk) protein kinases, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors Tec family (e.g., Tec, Btk, Itk/Emt/Tsk, Bmx, Txk/Rlk) protein kinases. These compounds have the general formula I:

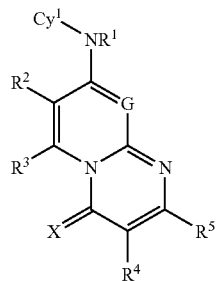

I or a pharmaceutically acceptable salt thereof, wherein $R^1$, $R^2$, $R^3$, $R^4$, $R^5$, G, $Cy^1$, and X are as defined below.

These compounds and pharmaceutically acceptable compositions thereof are useful for treating or preventing a variety of diseases, disorders or conditions, including, but not limited to, an autoimmune, inflammatory, proliferative, or hyperproliferative disease or an immunologically-mediated disease. The compositions are also useful in methods for preventing thrombin-induced platelet aggregation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention

The present invention relates to a compound of formula I:

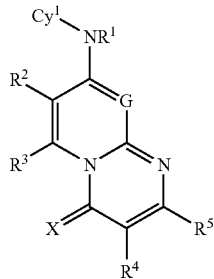

(I)

or a pharmaceutically acceptable salt thereof,
wherein $R^1$ is $-QR^X$; wherein Q is a bond or is a $C_1$-$C_6$ alkylidene chain wherein up to two methylene units of Q are optionally and independently replaced by $-CO-$, $-CS-$, $-COCO-$, $-CONR-$, $-CONRNR-$, $-CO_2-$, $-OCO-$, $-NRCO_2-$, $-O-$, $-NRCONR-$, $-OCONR-$, $-NRNR-$, $-NRNRCO-$, $-NRCO-$, $-S-$, $-SO$, $-SO_2-$, $-NR-$, $-SO_2NR-$, $-NRSO_2-$, $-NRSO_2NR-$, and each occurrence of $R^X$ is independently R', halogen, $NO_2$, or CN, provided $R^1$ is hydrogen or is bonded to the nitrogen atom through a carbon atom;

each occurrence of R is independently selected from hydrogen or an optionally substituted $C_{1-8}$ aliphatic group; and each occurrence of R' is independently selected from hydrogen or an optionally substituted group selected from $C_{1-8}$ aliphatic, $C_6$-$C_{10}$ aryl, a heteroaryl ring having 5-10 ring atoms, or a heterocyclyl ring having 3-10 ring atoms, or wherein R and R' taken together with the atom(s) to which they are bound, two occurrences of R taken together with the atom(s) to which they are bound, from an optionally substituted group together with the atom(s) to which they are bound, from an optionally substituted group selected from a 3-10 membered cycloalkyl ring, a $C_6$-$C_{10}$aryl ring, a heteroaryl ring having 5-10 ring atoms, or a heterocyclyl ring having 3-10 ring atoms;

$Cy^1$ is a 5-7-membered monocyclic aryl ring or an 8-10-membered bicyclic aryl ring having 0-3 heteroatoms independently selected from nitrogen, oxygen, or sulfur, or is a 3-8-membered saturated or partially unsaturated monocyclic ring having 0-3 heteroatoms independently selected from nitrogen, oxygen, or sulfur, wherein $Cy^1$ is optionally substituted with y occurrences of $-YR^Y$, wherein y is 0-5, Y is a bond or is a $C_1$-$C_6$ alkylidene chain wherein up to two methylene units of Y are optionally and independently replaced by $-CO-$, $-CS-$, $-COCO-$, $-CONR-$, $-CONRNR-$, $-CO_2-$, $-OCO-$, $-NRCO_2-$, $-O-$, $-NRCONR-$, $-OCONR-$, $-NRNR-$, $-NRNRCO-$, $-NRCO-$, $-S-$, $-SO$, $-SO_2-$, $-NR-$, $-SO_2NR-$, $-NRSO_2-$, $-NRSO_2NR-$, and each occurrence of $R^Y$ is independently R', halogen, $NO_2$, or CN;

$R^2$, $R^3$, $R^4$, and $R^5$ are each independently halogen, $-CN$, $-NO_2$, or $-VR^V$, or $R^2$ and $R^3$, or $R^4$ and $R^5$, taken together, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein any ring formed by $R^2$ and $R^3$ taken together is optionally substituted at one or more carbon or nitrogen atoms with m independent occurrences of $-WR^W$, or any ring formed by $R^4$ and $R^5$, taken together is optionally substituted at one or more carbon or nitrogen atoms with n independent occurrences of $Z-R^Z$, wherein m and n are each independently 0-5;

V, W, and Z are each independently a bond or is an optionally substituted $C_1$-$C_6$ alkylidene chain wherein up to two methylene units of V, W, or Z are optionally replaced by $-CO-$, $-CS-$, $-COCO-$, $-CONR-$, $-CONRNR-$, $-CO_2-$, $-OCO-$, $-NRCO_2-$, $-O-$, $-NRCONR-$, $-OCONR-$, $-NRNR-$, $-NRNRCO-$, $-NRCO-$, $-S-$, $-SO$, $-SO_2-$, $-NR-$, $-SO_2NR-$, $-NRSO_2-$, $-NRSO_2NR-$, and each occurrence of $R^V$, $R^W$, and $R^Z$ is independently R', halogen, $NO_2$, or CN;

X is O, S, or $[C(R^1)_2]_q$, where q is 1 or 2; and
G is N or $CR^6$, wherein $R^6$ is halogen, CN, $NO_2$, or $QR^X$, provided that:

when X is O; $R^1$ is hydrogen; $R^2$ is hydrogen, methyl, or bromine; $R^3$ is hydrogen; G is N; and $R^4$ and $R^5$, taken together, are unsubstituted phenyl; then $Cy^1$ is not unsubstituted phenyl, or phenyl substituted in the ortho position with $CO_2R'$ or CONRR'; and when X is O; $R^1$ is hydrogen; $R^2$ and $R^3$, taken together are unsubstituted phenyl; $R^4$ and $R^5$, taken together are unsubstituted phenyl; and G is N; then $Cy^1$ is not unsubstituted phenyl.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°;

—OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule, wherein one or more methylene units may optionally and independently be replaced with a group including, but not limited to, CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR.

As detailed above, in some embodiments, two independent occurrences of R° (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

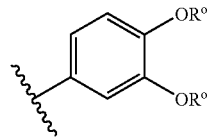

these two occurrences of R° are taken together with the oxygen atoms to which they are bound to form a fused 6-membered oxygen containing ring:

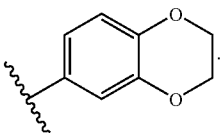

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

3. Description of Exemplary Compounds

As described generally above, $R^1$ is —$QR^X$; wherein Q is a bond or is a $C_1$-$C_6$ alkylidene chain wherein up to two methylene units of Q are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR—, —NRNRCO—, —NRCO—, —S—, —SO—, —$SO_2$—, —NR—, —$SO_2$NR—, —$NRSO_2$—, —$NRSO_2$NR—, and each occurrence of $R^X$ is independently R', halogen, $NO_2$, or CN, provided $R^1$ is hydrogen or is bonded to the nitrogen atom through a carbon atom. In certain embodiments, $R^1$ is hydrogen, —COR', CONRR', or is an optionally substituted $C_1$-$C_6$ alkyl group. In still other embodiments, for compounds of general formula I and classes and subclasses described herein, $R^1$ is hydrogen.

As described generally above, $Cy^1$ is a 5-7-membered monocyclic aryl ring or an 8-10-membered bicyclic aryl ring having 0-3 heteroatoms independently selected from nitrogen, oxygen, or sulfur, or is a 3-8-membered saturated or partially unsaturated monocyclic ring having 0-3 heteroatoms independently selected from nitrogen, oxygen, or sulfur, wherein $Cy^1$ is optionally substituted with y occurrences of —$YR^Y$. In certain embodiments, $Cy^1$ is a group selected from:

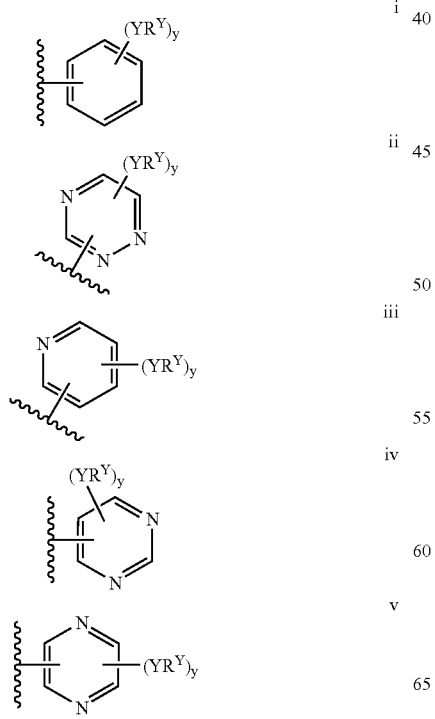

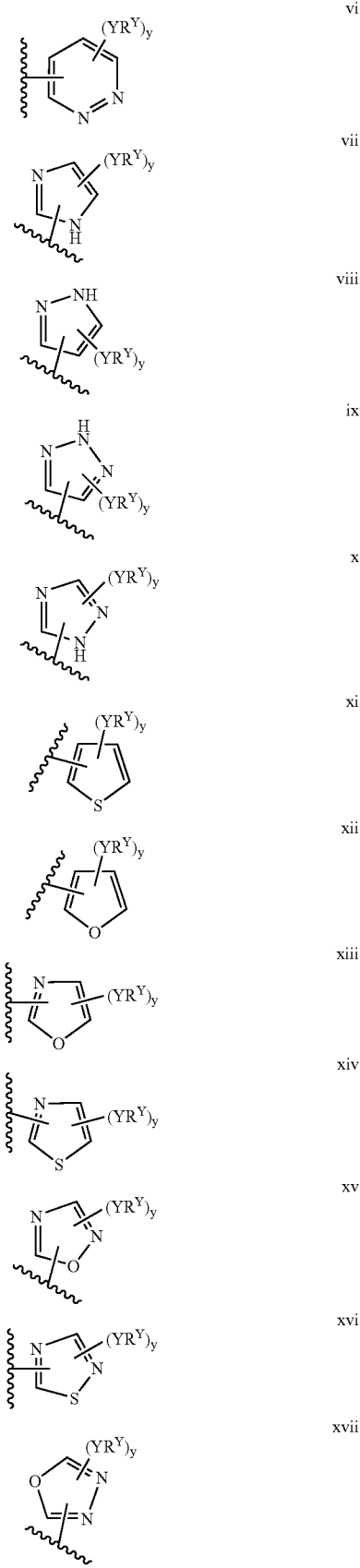

-continued

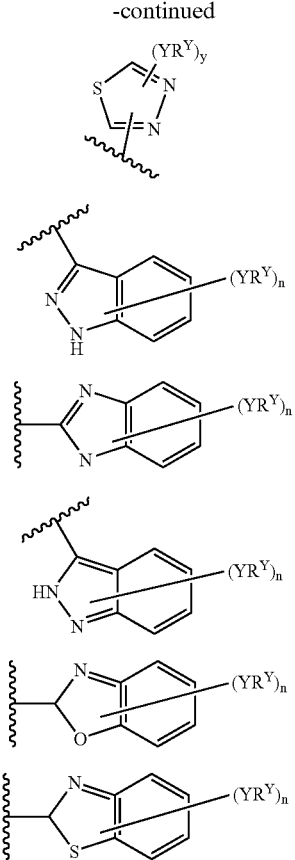

In other embodiments, Cy¹ is phenyl (i), pyridyl (iii), pyrimidinyl (iv), imidazolyl (vi), pyrazolyl (vii), triazolyl (x), thiazolyl (xiv), or indazole (xix) or (xxi). In still other embodiments, Cy¹ is phenyl (i) or pyrazolyl (vii).

It will be appreciated that, as described generally above, Cy¹ is optionally substituted at any substitutable carbon or nitrogen atom with y occurrences of —YR$^Y$, wherein y is 0-5, Y is a bond or is a $C_1$-$C_6$ alkylidene chain wherein up to two methylene units of Y are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR—, —NRNRCO—, —NRCO—, —S—, —SO—, —SO$_2$—, —NR—, —SO$_2$NR—, —NRSO$_2$—, —NRSO$_2$NR—, and each occurrence of R$^Y$ is independently R', halogen, NO$_2$, or CN. In some embodiments, each occurrence of —YR$^Y$, when present, is independently halogen, R', CN, NO$_2$, —N(R')$_2$, —CH$_2$N(R')$_2$, —(CH$_2$)$_2$N(R')$_2$, —(CH$_2$)$_3$N(R')$_2$, —OR', —CH$_2$OR', —(CH$_2$)$_2$O(R')$_2$, —(CH$_2$)$_3$O(R')$_2$, —SR', —CH$_2$SR', —(CH$_2$)$_2$S(R')$_2$, —(CH$_2$)$_3$S(R')$_2$, —COOR', —NRCOR', NRCOOR', —CON(R')$_2$, or —S(O)$_2$N(R')$_2$. In other embodiments, —YR$^Y$ groups are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl), —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or —YR$^Y$ groups are each independently an optionally substituted group selected from linear or branched $C_1$-$C_6$alkyl, $C_3$-$C_8$cycloalkyl, phenyl, phenyloxy, benzyl, benzyloxy, pyridyl, pyrimidinyl, thiophene, N-morpholinyl, N-piperidinyl, N-piperazinyl, or furanyl. In still other embodiments, y is 1 and YR$^Y$ is cyclopropyl, cyclobutyl, cyclopenyl, cyclohexyl, methyl, ethyl, n-propyl, isopropyl, n-butyl, phenyl, NH$_2$, (CH$_2$)$_3$OR', or (CH$_2$)$_2$N(R')$_2$.

As described generally above for compounds of formula I, R² and R³ are each independently halogen, —CN, —NO$_2$, or —VR$^V$, or R² and R³, taken together with the atoms to which they are bound, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur.

In certain embodiments, R² and R³ are each independently halogen, —CN, —NO$_2$, or —VR$^V$. In other embodiments, R² and R³ are each independently hydrogen, OR', SR', N(R')$_2$, —COR', NRCOR', NRSO$_2$R', —SO$_2$N(R')$_2$, or an optionally substituted group selected from C$_1$-C$_6$alkyl, or a 5- or 6-membered saturated, partially unsaturated, or fully unsaturated ring.

In certain embodiments, R² and R³, taken together with the atoms to which they are bound, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur. In certain other embodiments, R² and R³, taken together with the carbon atoms to which they are bound form an optionally substituted ring selected from one of the following groups:

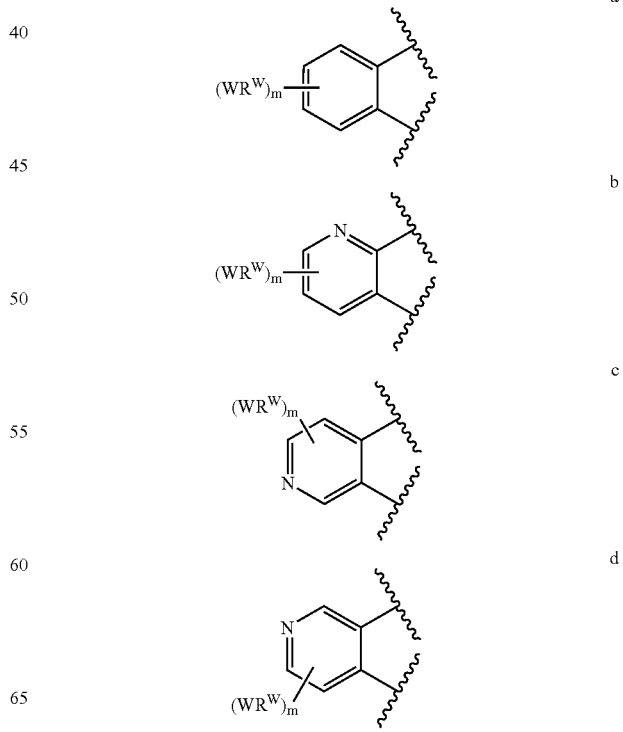

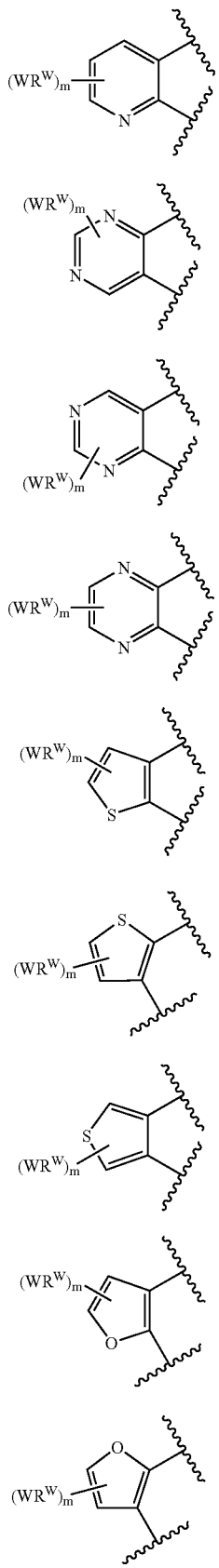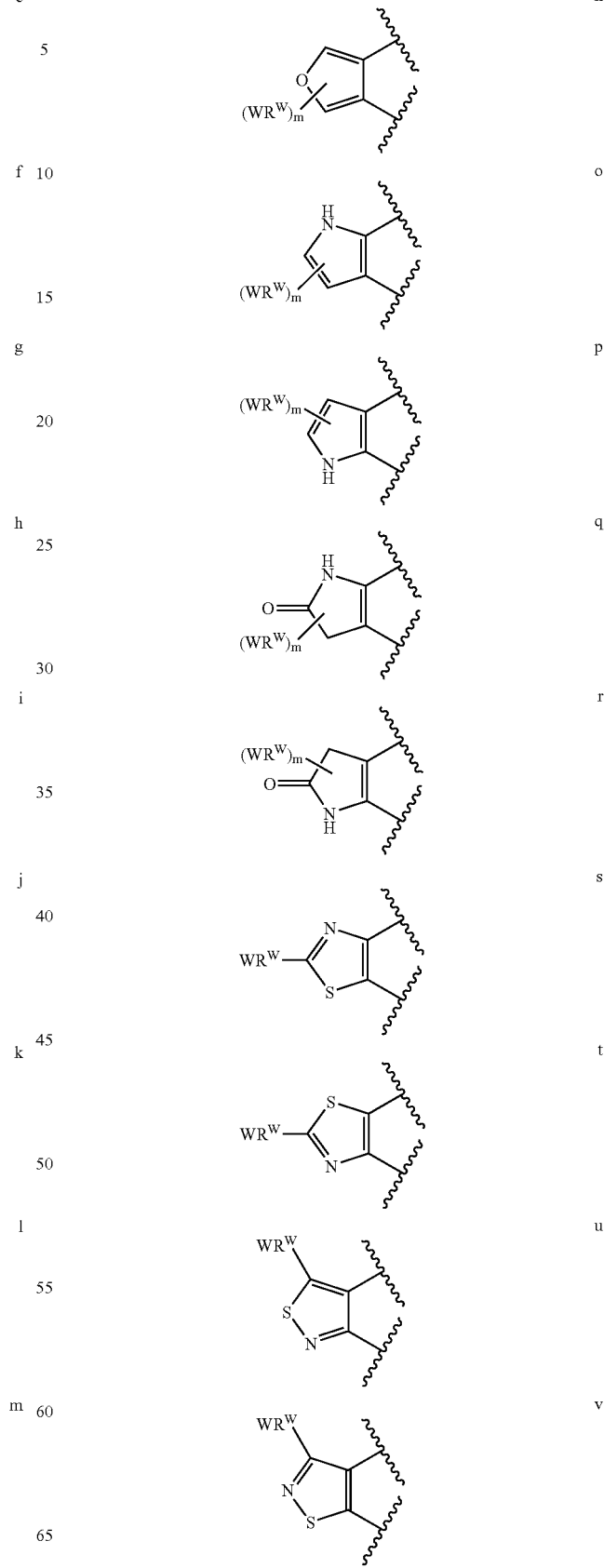

-continued
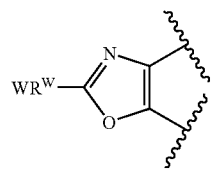 w
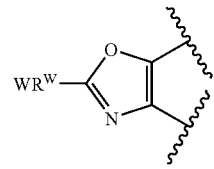 x
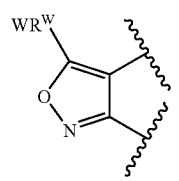 y
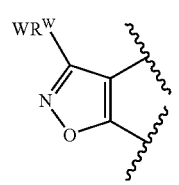 z
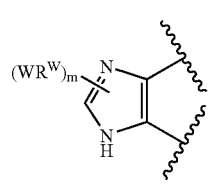 aa
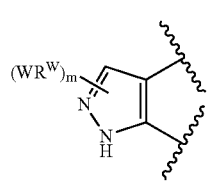 bb
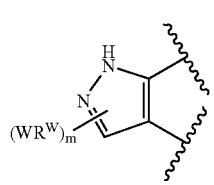 cc
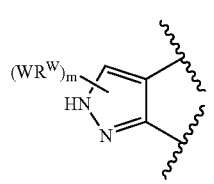 dd
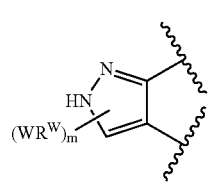 ee
-continued
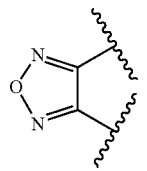 ff
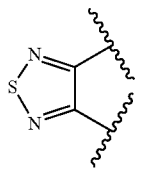 gg
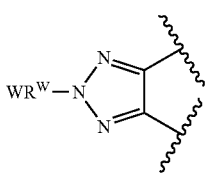 hh
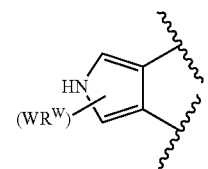 ii
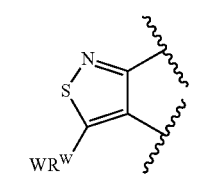 jj
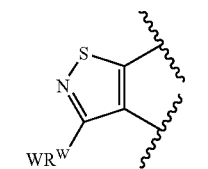 kk
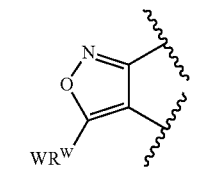 ll
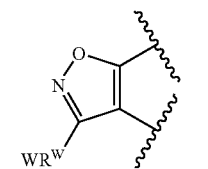 mm
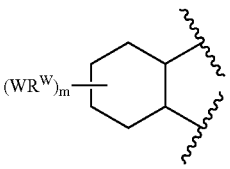 nn

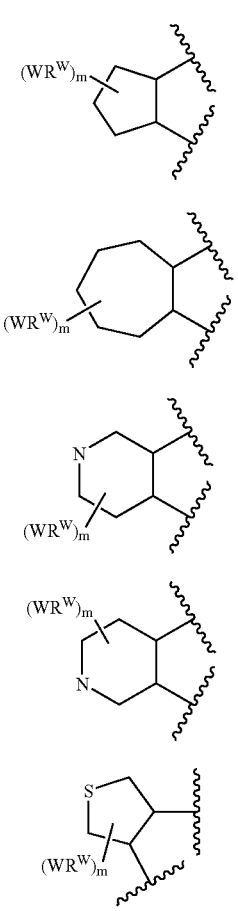

oo pp qq rr ss

In still other embodiments, $R^2$ and $R^3$, taken together with the carbon atoms to which they are bound form an optionally substituted 5- or 6-membered ring selected from phenyl (a), pyridyl (b, c, d, or e), cyclohexyl (nn), or cyclopentyl (oo).

It will be appreciated that any ring formed by $R^2$ and $R^3$ taken together is optionally optionally substituted at any substitutable carbon or nitrogen atom with m occurrences of —$WR^W$, wherein m is 0-5, W is a bond or is a $C_1$-$C_6$ alkylidene chain wherein up to two methylene units of W are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR, —NRNRCO—, —NRCO—, —S—, —SO, —$SO_2$—, —NR—, —$SO_2$NR—, —$NRSO_2$—, —$NRSO_2$NR—, and each occurrence of $R^W$ is independently R', halogen, $NO_2$, or CN. In some embodiments, each occurrence of —$WR^W$, when present, is independently halogen, R', CN, $NO_2$, —N(R')$_2$, —$CH_2$N(R')$_2$, —($CH_2$)$_2$N(R')$_2$, —($CH_2$)$_3$N(R')$_2$, —OR', —$CH_2$OR', —($CH_2$)$_2$O(R')$_2$, —($CH_2$)$_3$O(R')$_2$, —SR', —$CH_2$SR', —($CH_2$)$_2$S(R')$_2$, —($CH_2$)$_3$S(R')$_2$, —COOR', —NRCOR', NRCOOR', —CON(R')$_2$, or —S(O)$_2$N(R')$_2$. In other embodiments, —$WR^W$ groups are each independently F, Cl, Br, I, —CN, —COOMe, —COOH, —OH, $NH_2$, SH, —$SO_2NH_2$, —CON(CH$_3$)$_2$, —O($C_1$-$C_6$alkyl), —$CH_2$O($C_1$-$C_6$alkyl), —($CH_2$)$_2$O($C_1$-$C_6$alkyl), —($CH_2$)$_3$O($C_1$-$C_6$alkyl), —S($C_1$-$C_6$alkyl), —$CH_2$S($C_1$-$C_6$alkyl), —($CH_2$)$_2$S($C_1$-$C_6$alkyl), —($CH_2$)$_3$S($C_1$-$C_6$alkyl), —N($C_1$-$C_6$alkyl)$_2$, —$CH_2$N($C_1$-$C_6$alkyl)$_2$, —($CH_2$)$_2$N($C_1$-$C_6$alkyl)$_2$, —($CH_2$)$_3$N($C_1$-$C_6$alkyl)$_2$, wherein each $C_1$-$C_6$alkyl group is optionally substituted with R', —OR', —N(R')$_2$, —SR', —$SO_2$N(R')$_2$, —$NRSO_2$R', —CON(R')$_2$, or —NRCOR', or —$WR^W$ groups are each independently an optionally substituted group selected from $C_1$-$C_6$alkyl, $C_3$-$C_8$cycloalkyl, phenyl, phenyloxy, benzyl, benzyloxy, pyridyl, pyrimidinyl, thiophene, N-morpholinyl, N-piperidinyl, N-piperazinyl, or furanyl.

As described generally above, G is N or $CR^6$ wherein $R^6$ is halogen, CN, $NO_2$ or —$QR^X$. In some embodiments, G is CH or C($C_1$-$C_6$alkyl). In other embodiments G is N and compounds have the general formula II:

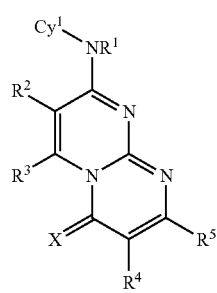

II

In other embodiments X is O and compounds have the general formula III:

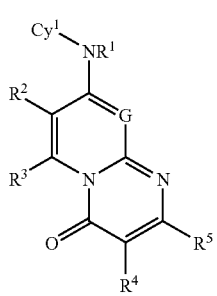

III

In still other embodiments X is O and G is N and compounds have the general formula IV:

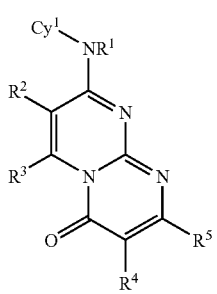

IV

As described generally above for compounds of formula I, $R^4$ and $R^5$ are each independently halogen, —CN, —$NO_2$, or —$VR^V$, or $R^4$ and $R^5$, taken together with the atoms to which they are bound, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur.

In certain embodiments, $R^4$ and $R^5$ are each independently halogen, —CN, —NO$_2$, or —VR$^V$. In other embodiments, $R^4$ and $R^5$ are each independently hydrogen, OR', SR', N(R')$_2$, —COR', NRCOR', NRSO$_2$R', —SO$_2$N(R')$_2$, or an optionally substituted group selected from C$_1$-C$_6$alkyl, or a 5- or 6-membered saturated, partially unsaturated, or fully unsaturated ring.

In certain embodiments, $R^4$ and $R^5$, taken together with the atoms to which they are bound, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur. In certain other embodiments, $R^4$ and $R^5$, taken together with the carbon atoms to which they are bound form an optionally substituted ring selected from one of the following groups:

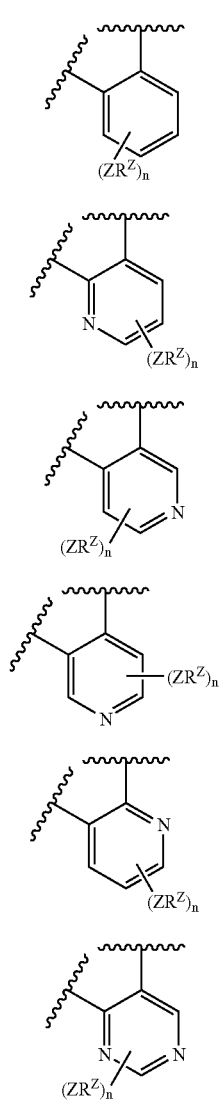

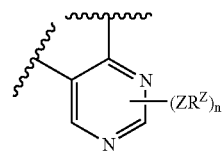

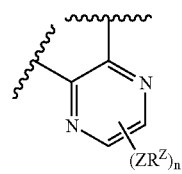

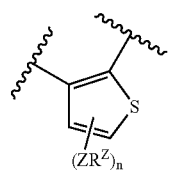

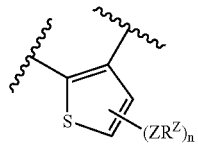

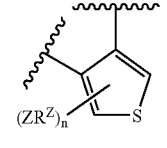

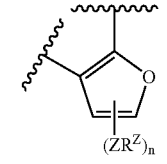

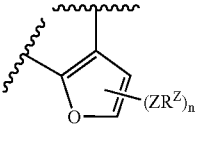

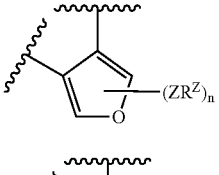

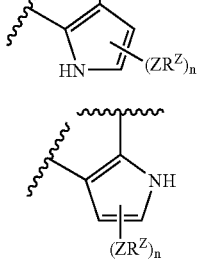

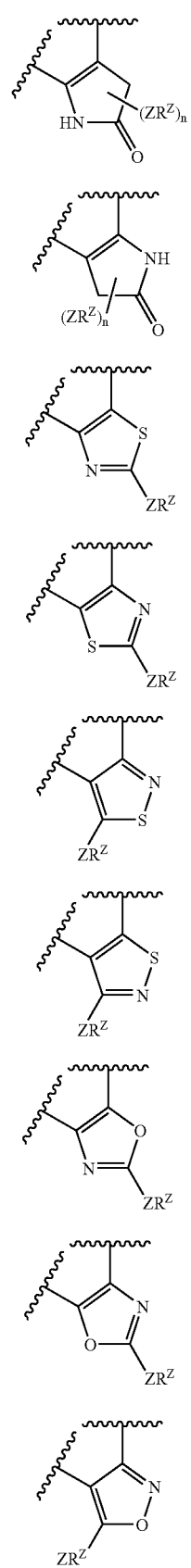
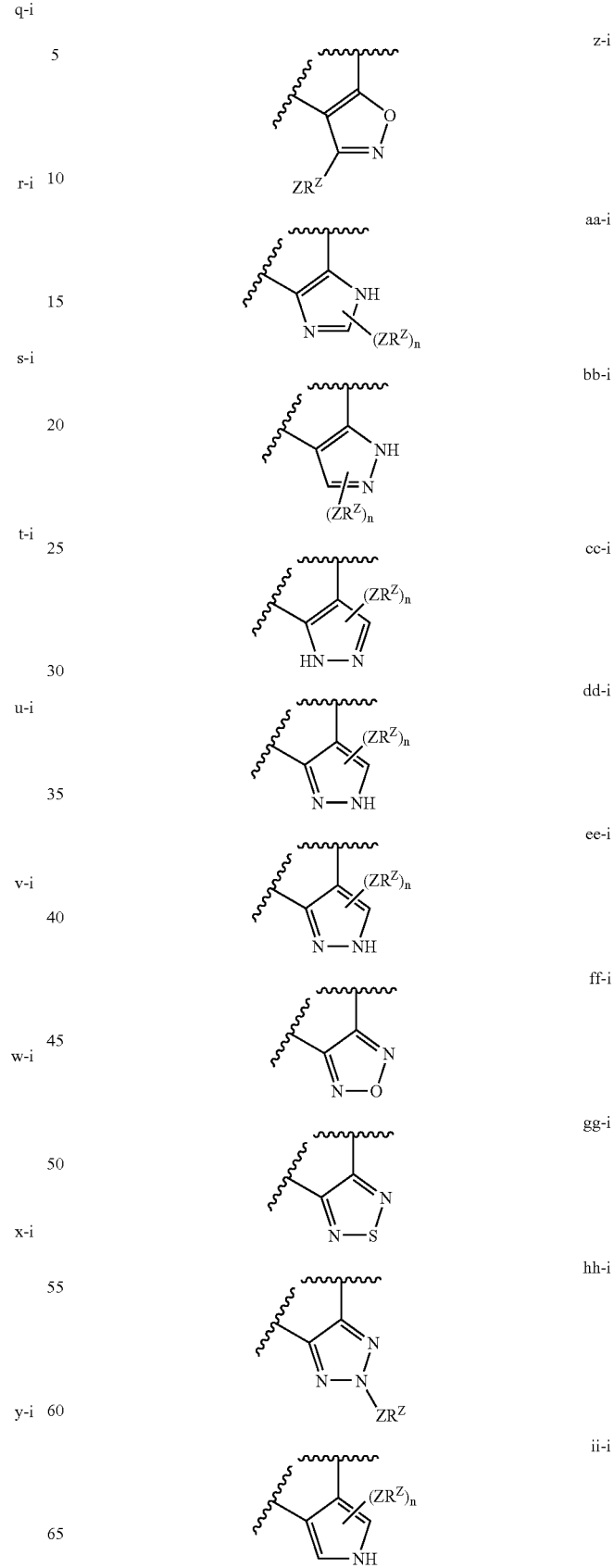

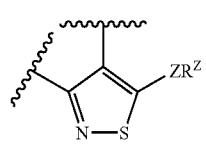
jj-i

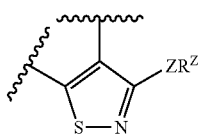
kk-i

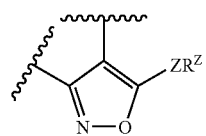
ll-i mm-i

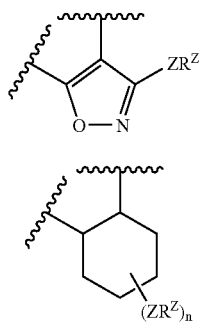
nn-i oo-i

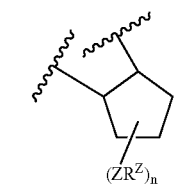

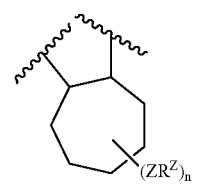

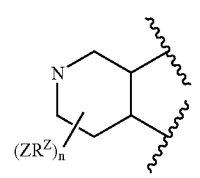
pp-i

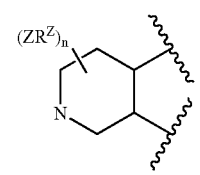
qq-i rr-i

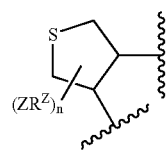
ss-i

In still other embodiments, $R^4$ and $R^5$, taken together with the carbon atoms to which they are bound form an optionally substituted 5- or 6-membered ring selected from phenyl (a-i), pyridyl (b-i, c-i, d-i, or e-i), cyclohexyl (nn-i), or cyclopentyl (oo-i).

It will be appreciated that any ring formed by $R^4$ and $R^5$ taken together is optionally optionally substituted at any substitutable carbon or nitrogen atom with n occurrences of —$ZR^Z$, wherein n is 0-5, Z is a bond or is a $C_1$-$C_6$ alkylidene chain wherein up to two methylene units of Z are optionally and independently replaced by —CO—, —CS—, —COCO—, —CONR—, —CONRNR—, —$CO_2$—, —OCO—, —$NRCO_2$—, —O—, —NRCONR—, —OCONR—, —NRNR—, —NRNRCO—, —NRCO—, —S—, —SO, —$SO_2$—, —NR—, —$SO_2$NR—, —$NRSO_2$—, —$NRSO_2$NR—, and each occurrence of $R^Z$ is independently R—, halogen, $NO_2$, or CN. In some embodiments, each occurrence of —$ZR^Z$, when present, is independently halogen, R—, CN, $NO_2$, —N(R')$_2$, —$CH_2$N(R')$_2$, —$(CH_2)_2$N(R')$_2$, —$(CH_2)_3$N(R')$_2$, —OR', —$CH_2$OR', —$(CH_2)_2$O(R')$_2$, —$(CH_2)_3$O(R')$_2$, —SR', —$CH_2$SR', —$(CH_2)_2$S(R')$_2$, —$(CH_2)_3$S(R')$_2$, —COOR', —NRCOR', NRCOOR', —CON(R')$_2$, or —$S(O)_2$N(R')$_2$. In other embodiments, —$ZR^Z$ groups are each independently F, Cl, Br, I, —CN, —COOMe, —COOH, —OH, $NH_2$, SH, —$SO_2NH_2$, —CON($CH_3$)$_2$, —O($C_1$-$C_6$alkyl), —$CH_2$O($C_1$-$C_6$alkyl), —$(CH_2)_2$O($C_1$-$C_6$alkyl), —$(CH_2)_3$O($C_1$-$C_6$alkyl), —S($C_1$-$C_6$alkyl), —$CH_2$S($C_1$-$C_6$alkyl), —$(CH_2)_2$S($C_1$-$C_6$alkyl), —$(CH_2)_3$S($C_1$-$C_6$alkyl), —N($C_1$-$C_6$alkyl)$_2$, —$CH_2$N($C_1$-$C_6$alkyl)$_2$, —$(CH_2)_2$N($C_1$-$C_6$alkyl)$_2$, —$(CH_2)_3$N($C_1$-$C_6$alkyl)$_2$, wherein each $C_1$-$C_6$alkyl group is optionally substituted with R', —OR', —N(R')$_2$, —SR', —$SO_2$N(R')$_2$, —$NRSO_2$R', —CON(R')$_2$, or —NRCOR', or —$ZR^Z$ groups are each independently an optionally substituted group selected from $C_1$-$C_6$alkyl, $C_3$-$C_8$cycloalkyl, phenyl, phenyloxy, benzyl, benzyloxy, pyridyl, pyrimidinyl, thiophene, N-morpholinyl, N-piperidinyl, N-piperazinyl, or furanyl.

In other embodiments, for compounds of formula I, G is N, X is O and $R^4$ and $R^5$, taken together form an optionally substituted phenyl group and compounds have formula V:

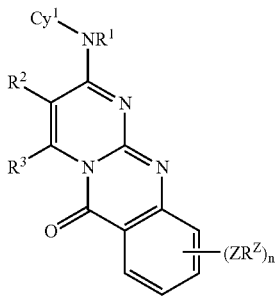

V

In some embodiments, $R^2$ and $R^3$ are each independently halogen, —CN, —NO$_2$, or —VR$^V$. In other embodiments, $R^2$ and $R^3$ are each independently hydrogen, OR', SR', N(R')$_2$, —COR', NRCOR', NRSO$_2$R', —SO$_2$N(R')$_2$, or an optionally substituted group selected from C$_1$-C$_6$alkyl, or a 5- or 6-membered saturated, partially unsaturated, or fully unsaturated ring.

In still other embodiments, $R^2$ and $R^3$, taken together with the atoms to which they are bound, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur. In certain other embodiments, $R^2$ and $R^3$, taken together with the carbon atoms to which they are bound form an optionally substituted ring selected from one of the following groups:

a
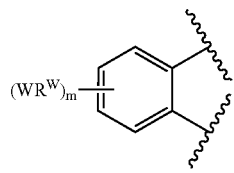

b
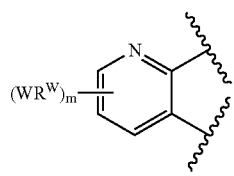

c
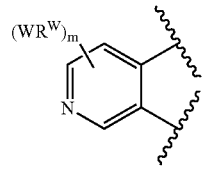

d
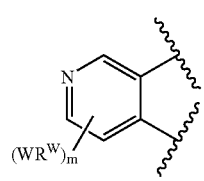

e
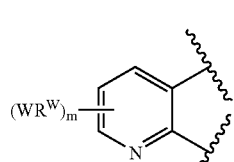

f
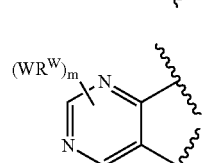

-continued g
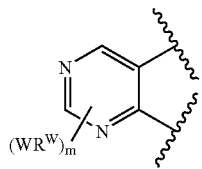

h
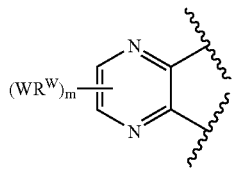

i
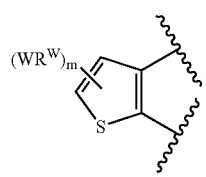

j
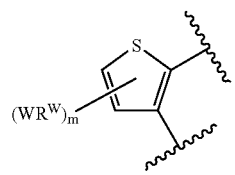

k
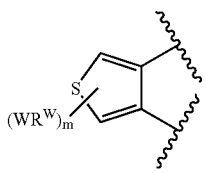

l
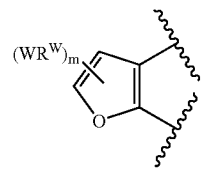

m
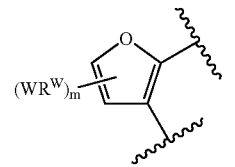

n
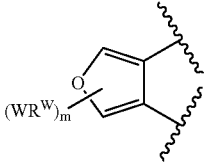

o

-continued
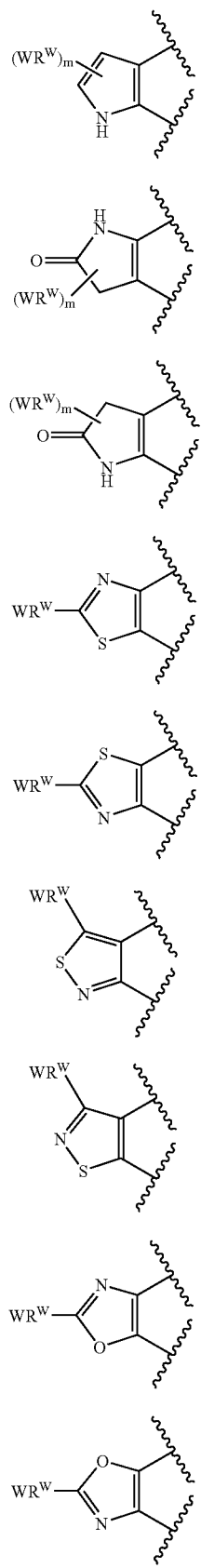
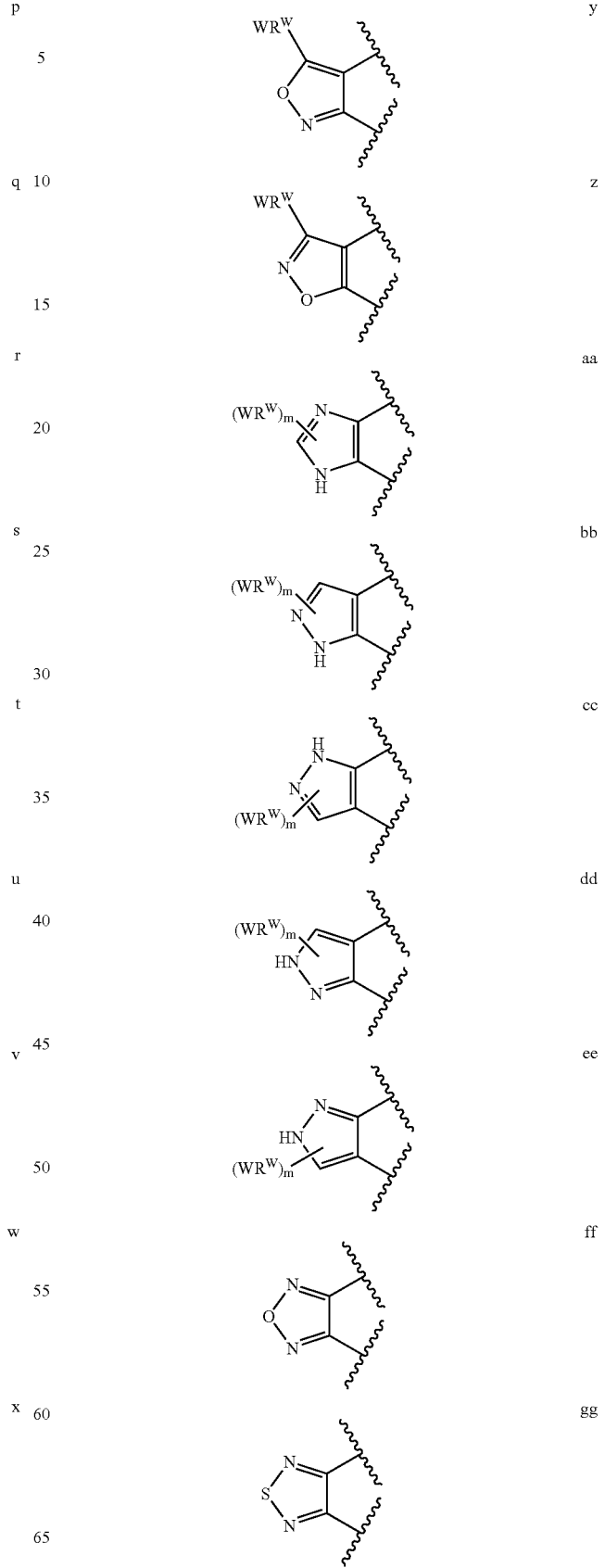

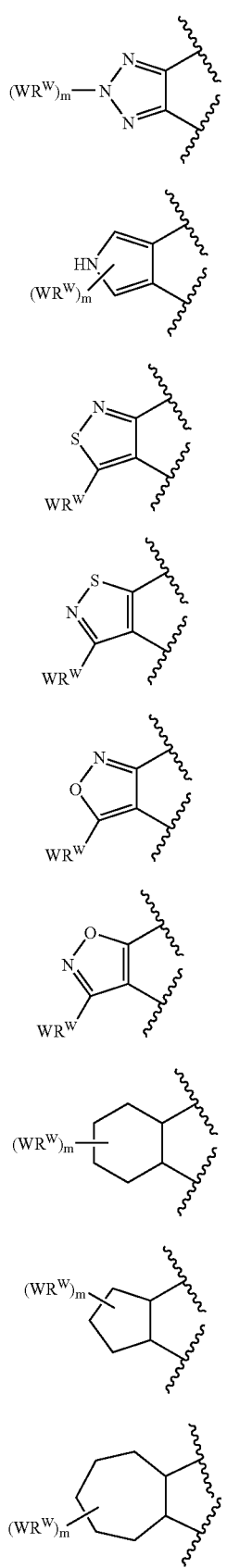

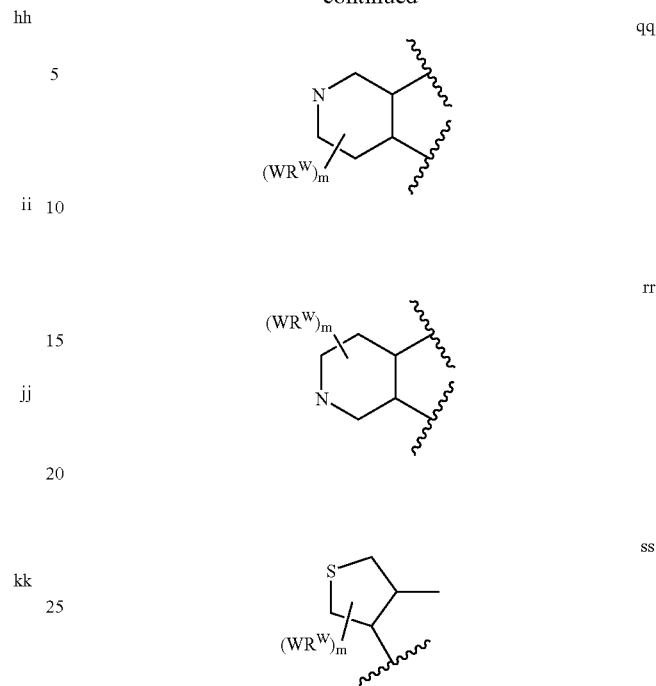

In still other embodiments, $R^2$ and $R^3$, taken together with the carbon atoms to which they are bound form an optionally substituted 5- or 6-membered ring selected from phenyl (a), pyridyl (b, c, d, or e), cyclohexyl (nn), or cyclopentyl (oo).

In yet other embodiments, $R^2$ and $R^3$, taken together with the carbon atoms to which they are bound form an optionally substituted phenyl, cyclopentyl, cyclohexyl, piperidine, pyrazolyl, or pyridyl group and compounds have formula V-A, V-B, V-C, V-D, V-E, or V-F:

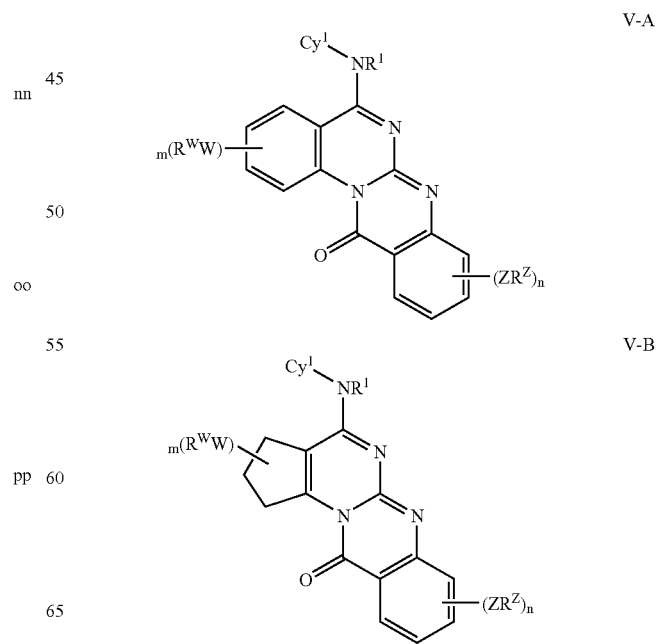

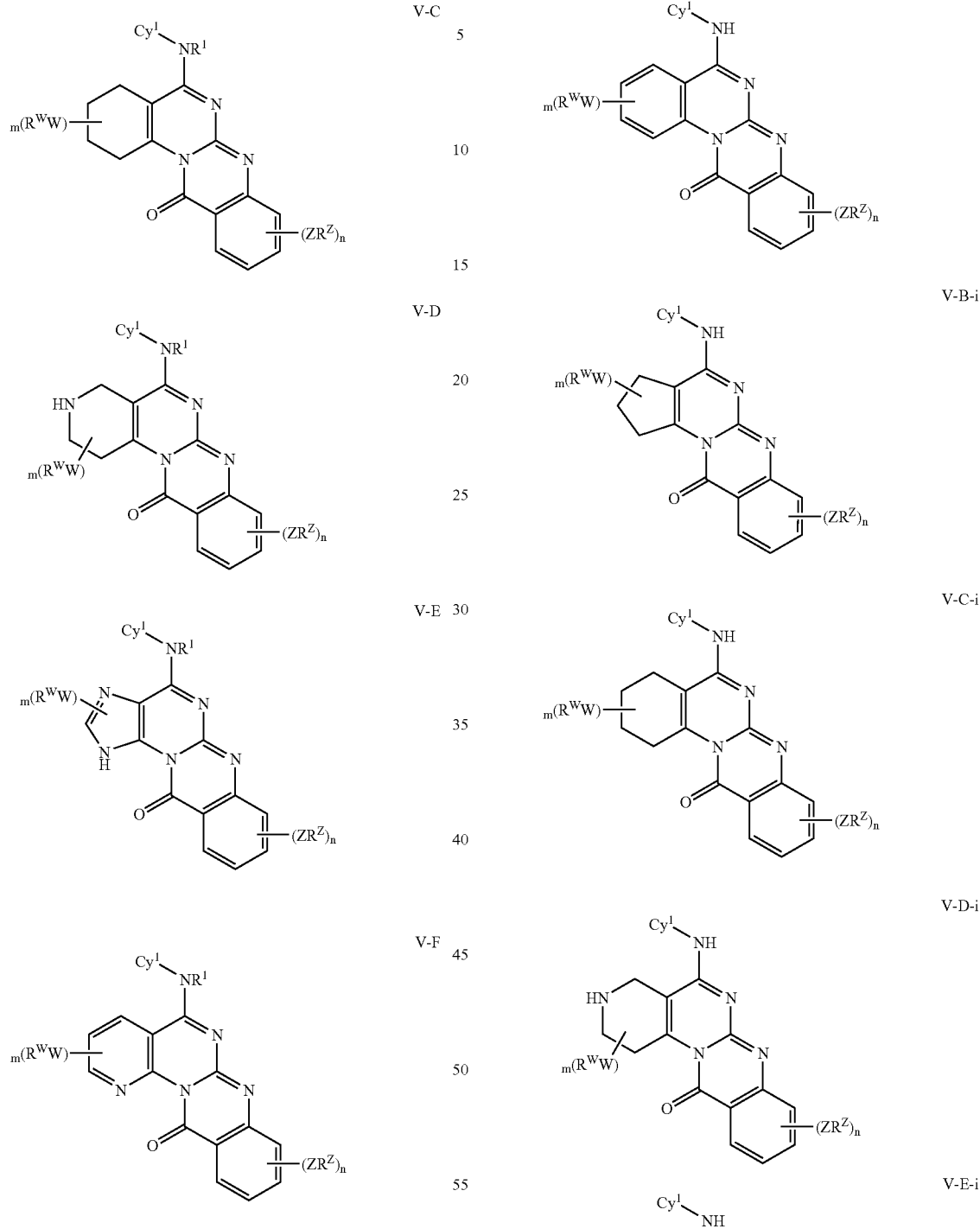

It will be appreciated that for compounds of formulae V-A, V-B, V-C, V-D, V-E, or V-F, Cy$^1$, R$^1$, WR$^W$, m, ZR$^Z$, and n are defined generally above and in subsets above and herein. In certain other embodiments, R$^1$ is hydrogen, —COR', CONRR', or is an optionally substituted C$_1$-C$_6$ alkyl group. In still other embodiments, R$^1$ is hydrogen and compounds of general formulae V-A-i, V-B-i, V-C-i, V-D-i, V-E-i, and V-F-i are provided.

-continued

V-F-i

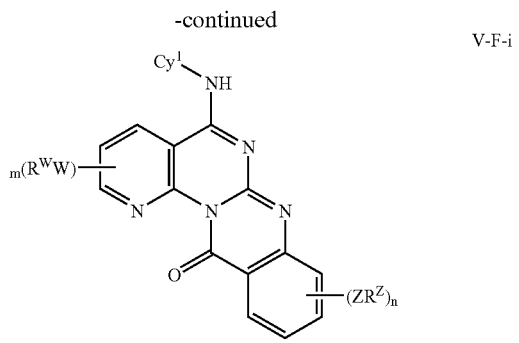

In certain other embodiments, $Cy^1$ phenyl (i), pyridyl (iii), pyrimidinyl (iv), imidazolyl (vi), pyrazolyl (vii), triazolyl (x), thiazolyl (xiv), or indazole (xix) or (xxi). In still other embodiments, $Cy^1$ is phenyl (i) or pyrazolyl (vii). In yet other embodiments, $Cy^1$ is pyrazolyl (vii).

As described generally above, $Cy^1$ is optionally substituted at any substitutable carbon or nitrogen atom with y occurrences of —$YR^Y$, wherein y is 0-5. In certain embodiments, y is 0, 1, or 2. In some embodiments, each occurrence of —$YR^Y$, when present, is independently halogen, R', CN, NO$_2$, —N(R')$_2$, —CH$_2$N(R')$_2$, —(CH$_2$)$_2$N(R')$_2$, —(CH$_2$)$_3$N(R')$_2$, —OR', —CH$_2$OR', —(CH$_2$)$_2$O(R')$_2$, —(CH$_2$)$_3$O(R')$_2$, —SR', —CH$_2$SR', —(CH$_2$)$_2$S(R')$_2$, —(CH$_2$)$_3$S(R')$_2$, —COOR', —NRCOR', NRCOOR', —CON(R')$_2$, or —S(O)$_2$N(R')$_2$. In other embodiments, —$YR^Y$ groups are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl)$_2$, —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or —$YR^Y$ groups are each independently an optionally substituted group selected from C$_1$-C$_6$alkyl, phenyl, phenyloxy, benzyl, benzyloxy, pyridyl, pyrimidinyl, thiophene, N-morpholinyl, N-piperidinyl, N-piperazinyl, or furanyl. In other embodiments, y is 0 or 1 and —$YR^Y$ groups, when present, are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl), —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or $YR^Y$ groups are each independently an optionally substituted group selected from linear or branched C$_1$-C$_6$alkyl, C$_3$-C$_8$cycloalkyl, phenyl, phenyloxy, benzyl, benzyloxy, pyridyl, pyrimidinyl, thiophene, N-morpholinyl, N-piperidinyl, N-piperazinyl, or furanyl. In still other embodiments, y is 1 and $YR^Y$ is cyclopropyl, cyclobutyl, cyclopenyl, cyclohexyl, methyl, ethyl, n-propyl, isopropyl, n-butyl, phenyl, NH$_2$, (CH$_2$)$_3$OR', or (CH$_2$)$_2$N(R')$_2$.

In still other embodiments, m and n are each independently 0, 1, or 2. In some embodiments, each occurrence of —$WR^W$ and —$ZR^Z$, when present, are each independently halogen, R', CN, NO$_2$, —N(R')$_2$, —CH$_2$N(R')$_2$, —(CH$_2$)$_2$N(R')$_2$, —(CH$_2$)$_3$N(R')$_2$, —OR', —CH$_2$OR', —(CH$_2$)$_2$O(R')$_2$, —(CH$_2$)$_3$O(R')$_2$, —SR', —CH$_2$SR', —(CH$_2$)$_2$S(R')$_2$, —(CH$_2$)$_3$S(R')$_2$, —COOR', —NRCOR—, NRCOOR—, —CON(R')$_2$, or —S(O)$_2$N(R')$_2$. In other embodiments, —$WR^W$ and —$ZR^Z$ groups are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl), —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or —$WR^W$ and —$ZR^Z$ groups are each independently an optionally substituted group selected from C$_1$-C$_6$alkyl, phenyl, phenyloxy, benzyl, benzyloxy, pyridyl, pyrimidinyl, thiophene, N-morpholinyl, N-piperidinyl, N-piperazinyl, or furanyl. In other embodiments, m and n are each independently 0 or 1 and —$WR^W$ and —$ZR^Z$ groups, when present, are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl), —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or —$WR^W$ and —$ZR^Z$ groups are each independently an optionally substituted group selected from C$_1$-C$_6$alkyl, C$_3$-C$_8$cycloalkyl, phenyl, phenyloxy, benzyl, benzyloxy, pyridyl, pyrimidinyl, thiophene, N-morpholinyl, N-piperidinyl, N-piperazinyl, or furanyl.

Representative examples of compounds of formula I are depicted in Table 1.

TABLE 1

Examples of Compounds of Formula I:

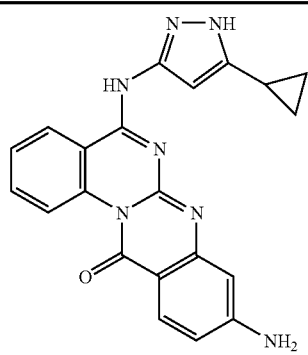

I-1

TABLE 1-continued
Examples of Compounds of Formula I:
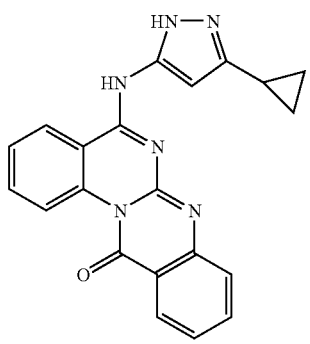
I-2
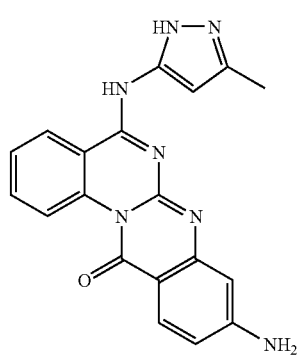
I-3
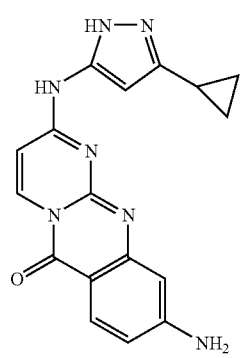
I-4
TABLE 1-continued
Examples of Compounds of Formula I:
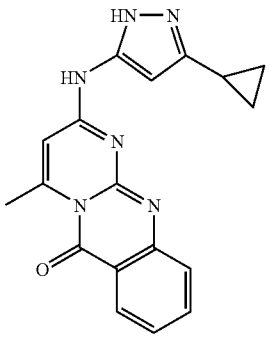
I-5
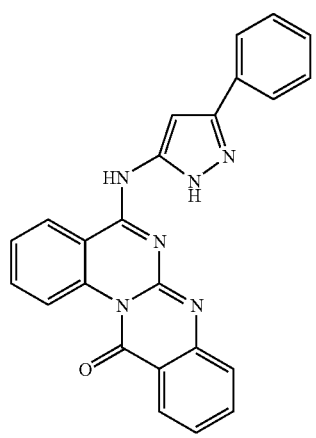
I-6
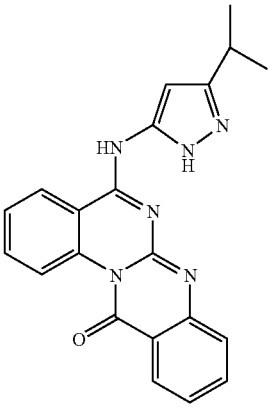
I-7

TABLE 1-continued
Examples of Compounds of Formula I:
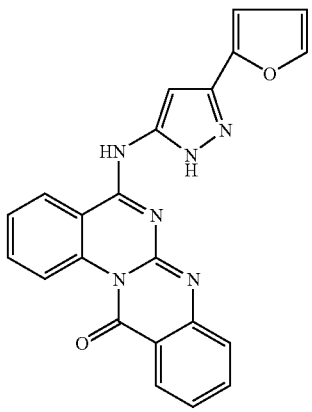
I-8
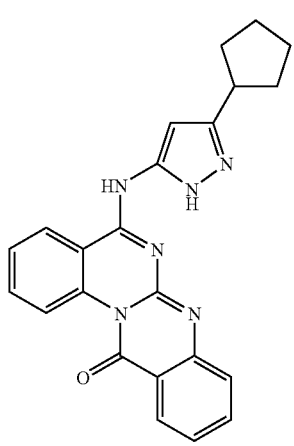
I-9
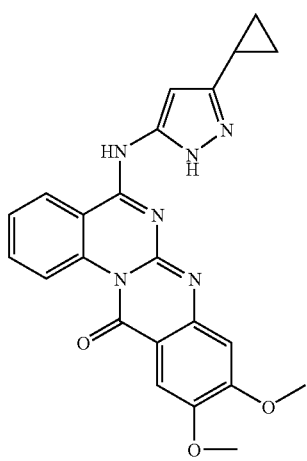
I-10
TABLE 1-continued
Examples of Compounds of Formula I:
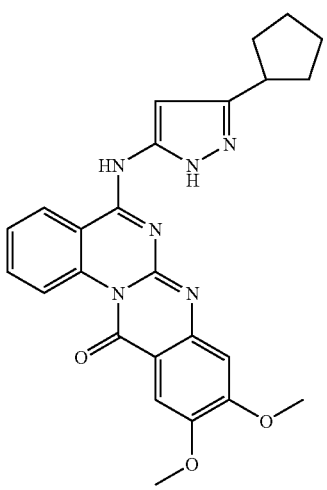
I-11
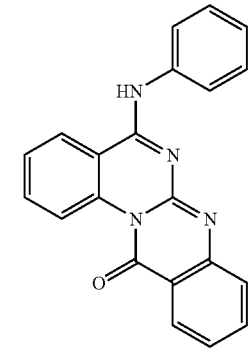
I-12
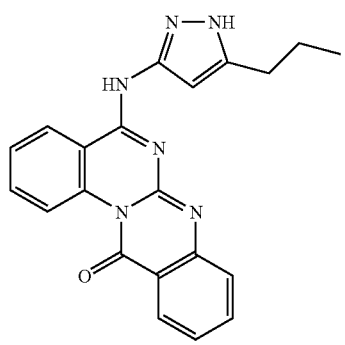
I-13

TABLE 1-continued
Examples of Compounds of Formula I:
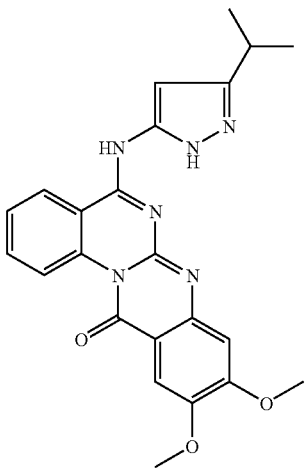
I-14
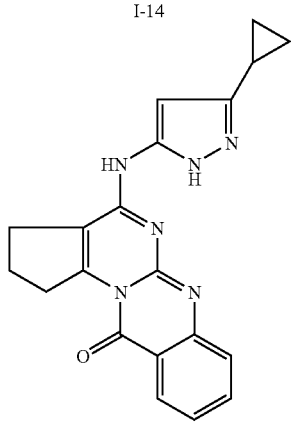
I-15
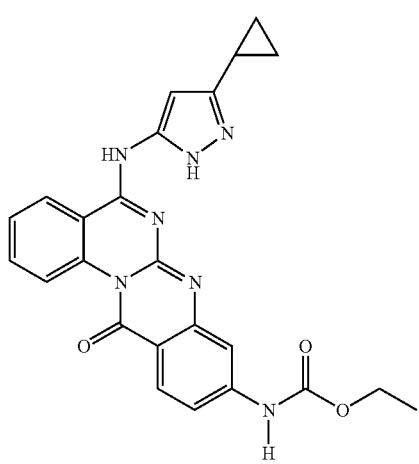
I-16
TABLE 1-continued
Examples of Compounds of Formula I:
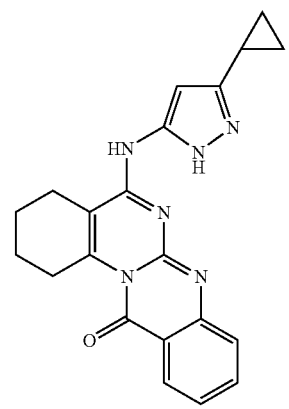
I-17
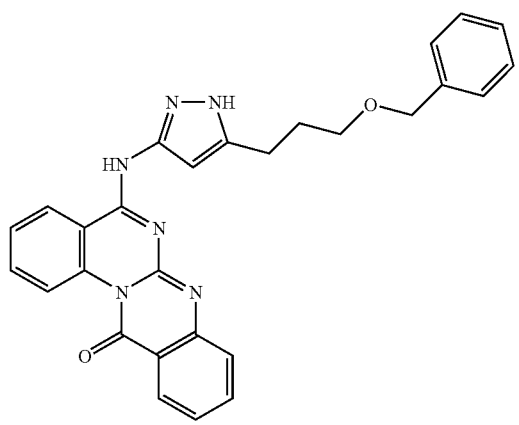
I-18
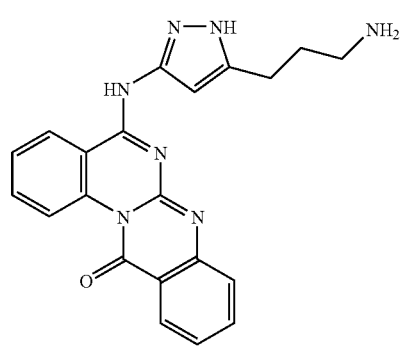
I-19

TABLE 1-continued
Examples of Compounds of Formula I:
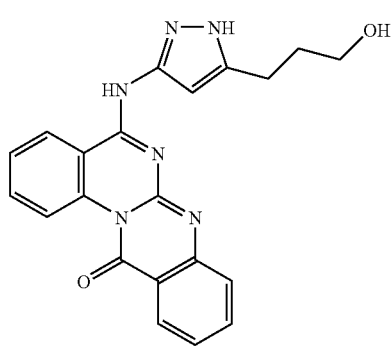
I-20
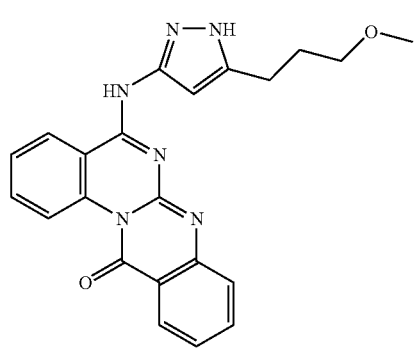
I-21
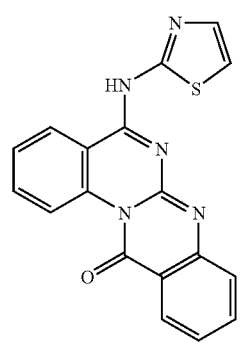
I-22
TABLE 1-continued
Examples of Compounds of Formula I:
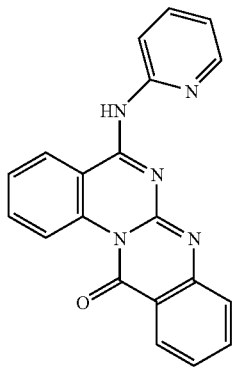
I-23
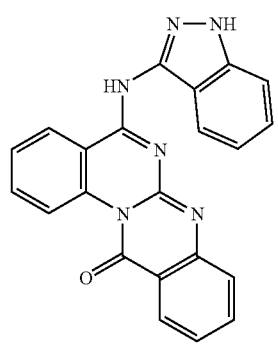
I-24
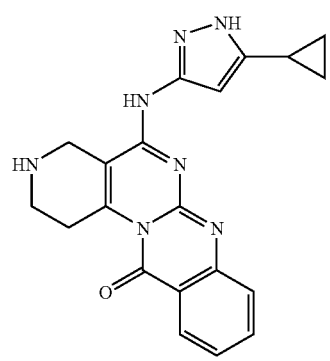
I-25

TABLE 1-continued

Examples of Compounds of Formula I:

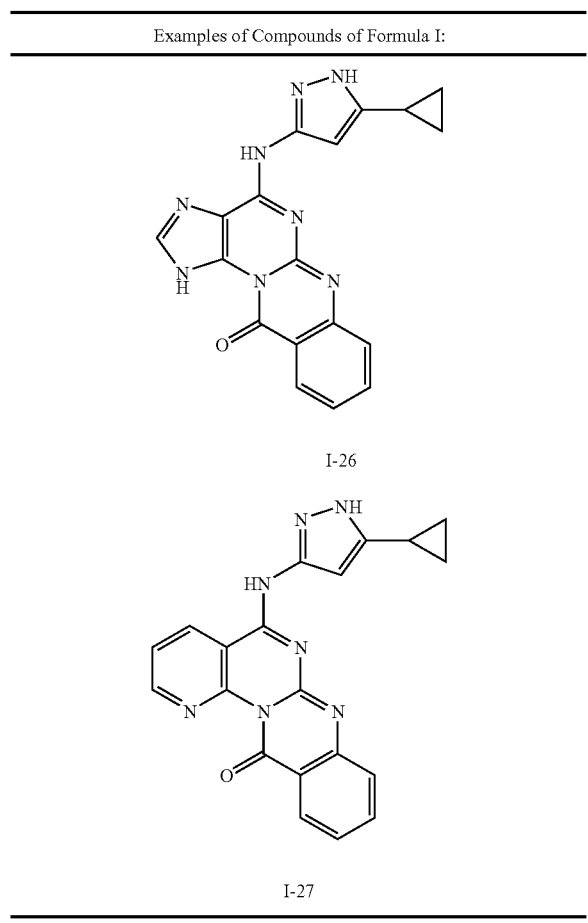

I-26

I-27

4. General Synthetic Methodology

The compounds of this invention may be prepared in general by methods known to those skilled in the art for analogous compounds, as illustrated by the general scheme below, and the preparative examples that follow.

Scheme I

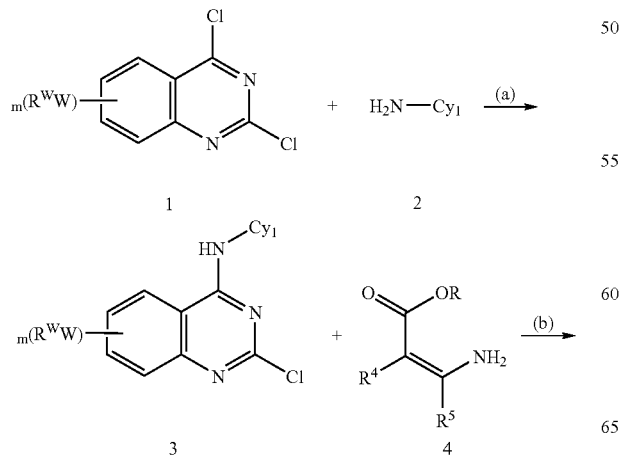

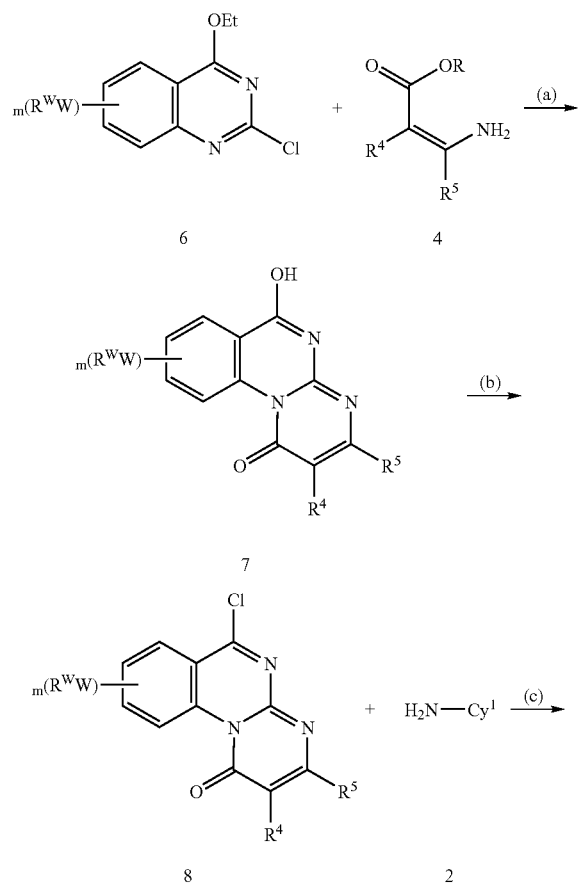

Reagents and conditions: (a) Et$_3$N, EtOH, r.t.; (b) 130° C., 3 hours.

Scheme I above shows a general synthetic route that is used for preparing the compounds 5 of this invention when Cy$^1$, R$^4$ and R$^5$ is as described above. The dichloroquinazoline 1 may be prepared by methods well known to those skilled in the art. Intermediate 3 is prepared according the scheme I step (a). Compound 3 is treated with aminoester 4 according to step (b). This reaction is amenable to a variety of aminoesters to form compounds of formula 5.

Scheme II

-continued

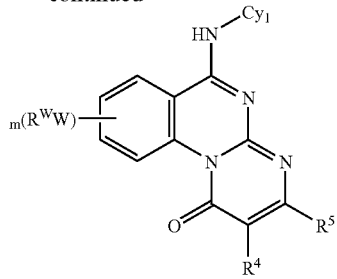

5

Reagents and conditions: (a) heat, 15 min.; (b) SOCl₂, rfx., 2 hours; (c) 50° C., Et₃N, THF/IPA(1:1), 4 hours or Pd₂(dba)₃, Xantphos, Na₂CO₃, dioxane/toluene (1:1), 100° C., 17 hours.

Scheme II above shows an alternative synthetic route which has been used for preparing compounds of formula 5 of this invention when $Cy^1$, $R^4$ and $R^5$ is as described above. The 2-chloro-4-ethoxyquinazoline 6 may be prepared by methods described by Lange et al, *J. Am. Chem. Soc.,* 1930, 52, 3696. Intermediate 8 is prepared by methods substantially similar to those described by Butler et al, *J. Chem. Soc.;* 1959, 1512 according to scheme II steps (a) and (b). Intermediate 8 is treated with amines of formula 2 according to step (c) in some cases by methods substantially similar to those described by Jingjun Y, et al., *Organic Letters,* 2002, 4, 3481. This reaction is amenable to a variety of $Cy^1$—$NH_2$ to form compounds of formula 5.

Scheme III

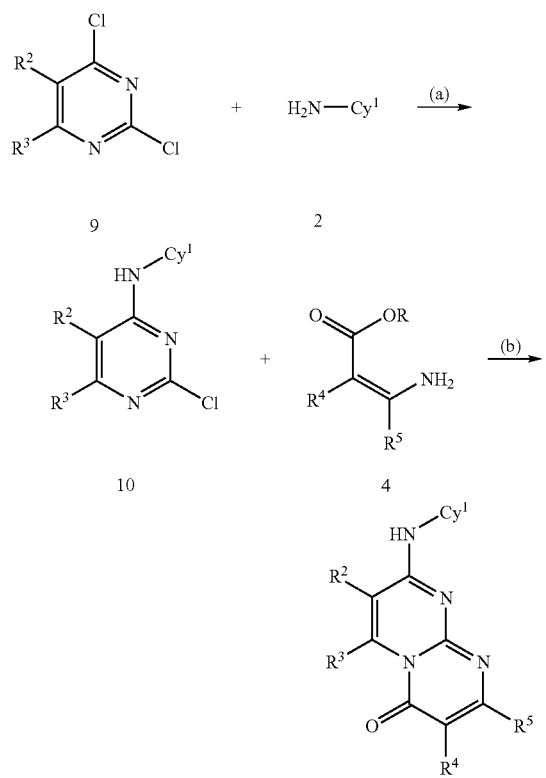

Reagents and conditions: (a) Et₃N, EtOH, 120° C., 24 hours; (b) 135° C., 4 hours.

Scheme III above shows another general synthetic route which has been used for preparing the compounds 11 of this invention when $Cy^1$, $R^2$, $R^3$, $R^4$ and $R^5$ is as described above. The formation of the dichloropyrimidine derivatives 9 is achieved by using methods well known for those skilled in the art. Intermediate 10 is prepared according the scheme III step (a). Compound 10 is treated with aminoesters 4 according to step (b). This reaction is amenable to a variety of aminoesters 4 to form compounds of formula 11.

Scheme IV

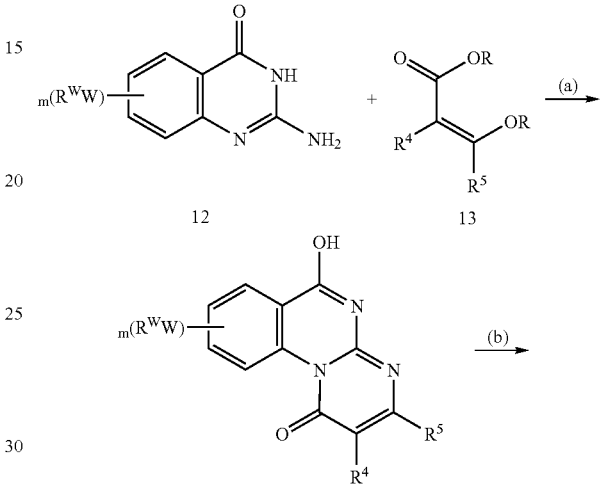

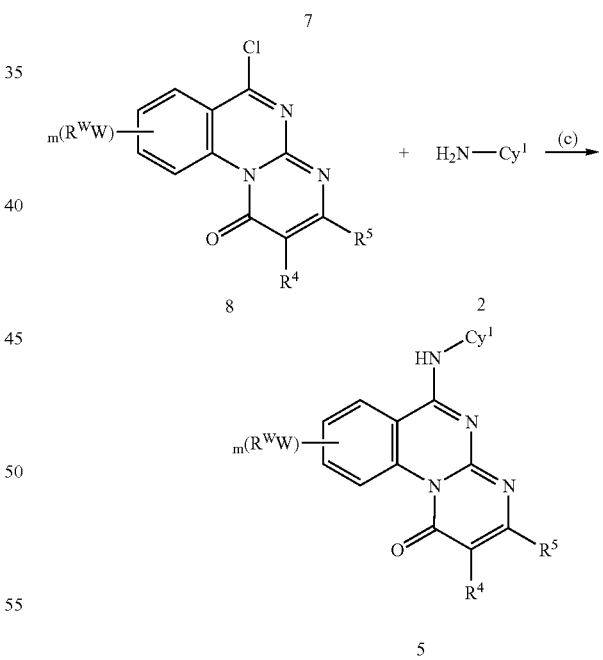

Reagents and conditions: (a) heat, 15 min.; (b) SOCl₂, rfx., 2 hours; (c) 50° C., Et₃N, THF/IPA(1:1), 4 hours or Pd₂(dba)₃, Xantphos, Na₂CO₃, dioxane/toluene (1:1), 100° C., 17 hours Scheme IV above shows an alternative synthetic route which has been used for preparing compounds of formula 5 of this invention when $Cy^1$, $R^4$ and $R^5$ is as described above. Intermediate 7 is alternatively prepared by methods substantially similar to those described by Deady et al, *J. Heterocyclic. Chem.;* 1989, 26, 161 according to scheme IV step (a).

Intermediate 8 is treated with amines of formula 2 according to step (c). This reaction is amenable to a variety of $Cy^1$—$NH_2$ to form compounds of formula 5.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Tec family (e.g., Tec, Btk, Itk/Emt/Tsk, Bmx, Txk/Rlk) protein kinases kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compound disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a Tec family (e.g., Tec, Btk, Itk/Emt/Tsk, Bmx, Txk/Rlk)-mediated diseases is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for a Tec family (e.g., Tec, Btk, Itk/Emt/Tsk, Bmx, Txk/Rlk)-mediated disease. The compounds and compositions, according to the method of the present invention, may be administered using any amount and any route of administration effective for treating or lessening the severity of a Tec family (e.g., Tec, Btk, Itk/Emt/Tsk, Bmx, Txk/Rlk)-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), banally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of Tec family (e.g., Tec, Btk, Itk/Emt/Tsk, Bmx, Txk/Rlk) kinase, and thus, without wishing to be bound by any particular theory, the compounds and compositions are particularly useful for treating or lessening the severity of a disease, condition, or disorder where activation of one or more of a Tec family (e.g., Tec, Btk, Itk/Emt/Tsk, Bmx, Txk/Rlk) kinase is implicated in the disease, condition, or disorder. When activation of Tec family (e.g., Tec, Btk, Itk/Emt/Tsk, Bmx, Txk/Rlk) is implicated in a particular disease, condition, or disorder, the disease, condition, or disorder may also be referred to as a "Tec family (e.g., Tec, Btk, Itk/Emt/Tsk, Bmx, Txk/Rlk)-mediated disease" or disease symptom. Accordingly, in another aspect, the present invention provides a method for treating or lessening the severity of a disease, condition, or disorder where activation or one or more of Tec family (e.g., Tec, Btk, Itk/Emt/Tsk, Bmx, Txk/Rlk) is implicated in the disease state.

The activity of a compound utilized in this invention as an inhibitor of a Tec family (e.g., Tec, Btk, Itk/Emt/Tsk, Bmx, Txk/Rlk) kinase may be assayed in vitro, in vivo or in a cell line. In vitro assays include assays that determine inhibition of either the phosphorylation activity or ATPase activity of activated Tec family (e.g., Tec, Btk, Itk/Emt/Tsk, Bmx, Txk/Rlk) kinase. Alternate in vitro assays quantitate the ability of the inhibitor to bind to a Tec family (e.g., Tec, Btk, Itk/Emt/Tsk, Bmx, Txk/Rlk) kinase. Inhibitor binding may be measured by radiolabelling the inhibitor prior to binding, isolating the inhibitor/Tec family (e.g., Tec, Btk, Itk/Emt/Tsk, Bmx, Txk/Rlk), complex and determining the amount of radiolabel bound. Alternatively, inhibitor binding may be determined by running a competition experiment where new inhibitors are incubated with a Tec family (e.g., Tec, Btk, Itk/Emt/Tsk, Bmx, Txk/Rlk) kinase bound to known radioligands.

The term "measurably inhibit", as used herein means a measurable change in a Tec family (e.g., Tec, Btk, Itk/Emt/Tsk, Bmx, Txk/Rlk) kinase activity between a sample comprising said composition and a Tec family (e.g., Tec, Btk, Itk/Emt/Tsk, Bmx, Txk/Rlk) kinase and an equivalent sample comprising a Tec family (e.g., Tec, Btk, Itk/Emt/Tsk, Bmx, Txk/Rlk) kinase in the absence of said composition.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, Tec family tyrosine kinases-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, Tec family tyrosine kinases diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases-mediated conditions also include diseases of the bone and joints including; without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Tec family tyrosine kinases-mediated conditions also include those diseases and disorders of other tissues and systemic disease, including, without limitation, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etopodie, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Tec family (e.g., Tec, Btk, Itk/Emt/Tsk, Bmx, Txk/Rlk) activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Tec family (e.g., Tec, Btk, Itk/Emt/Tsk, Bmx, Txk/Rlk) kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, The term "Rt(min)" refers to the HPLC retention time, in minutes, associated with the compound. Unless otherwise indicated, the HPLC method utilized to obtain the reported retention time is as follows:
 Column: Ace 5 C8, 15 cm×4.6 mm id
 Gradient: 0-100% acetonitrile+methanol (50:50) (20 mM Tris phosphate at pH 7.0)
 Flow rate: 1.5 ml/min
 Detection: 225 nm Example 1

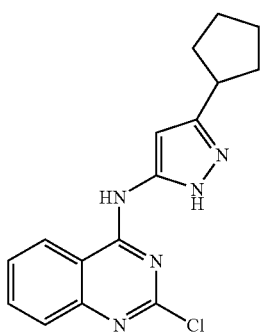

(2-Chloro-quinazolin-4-yl)-(5-cyclopentyl-2H-pyrazol-3-yl)-amine 2,4-Dichloroquinazoline (0.657 g, 3.3 mmol) in ethanol (9 ml) was treated with 3-amino-5-cyclopentyl pyrazole (0.5 g, 3.3 mmol) and triethylamine (0.46 ml, 3.3 mmol) and stirred overnight at room temperature. The mixture was filtered and the solid washed with ethanol to give (2-chloro-quinazolin-4-yl)-(5-cyclopentyl-2H-pyrazol-3-yl)-amine as colourless crystals (684 mg, 66%).

MS (ES+) 313

δH (d6 DMSO) 1.55-1.80 (6H, m), 2.03-2.13 (2H, m), 3.06-3.13 (1H, m), 6.60 (1H, s), 7.60 (1H, t), 7.70 (1H, d), 7.87 (1H, t), 8.64 (1H, d), 10.77 (1H, s), 12.37 (1H, s).

Example 2

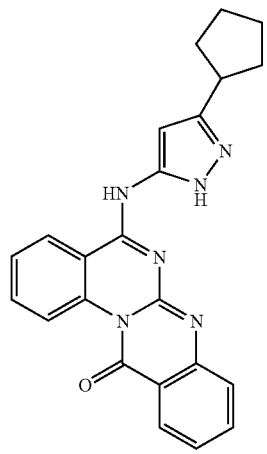

5-(5-Cyclopentyl-2H-pyrazol-3-ylamino)-quinazolino[3,2-a]quinazolin-12-one (2-Chloro-quinazolin-4-yl)-(5-cyclopentyl-2H-pyrazol-3-yl)-amine (0.1 g, 0.319 mmol) and methyl anthranilate (0.124 ml, 0.957 mmol) was stirred at 130° C. for 3 hours. The reaction mixture was suspended in methanol and added to a mixture of ethyl acetate and dilute aqueous sodium bicarbonate. The mixture was extracted with ethyl acetate and the extracts dried over magnesium sulphate and concentrated. The residue was purified by flash chromatography on silica gel eluting with 50% ethyl acetate/petrol to give a yellow glass (95 mg). This was dissolved in methanol and treated with 4M HCl/dioxane to give 5-(5-Cyclopentyl-2H-pyrazol-3-ylamino)-quinazolino[3,2-a]quinazolin-12-one hydrochloride as very pale yellow crystals (85 mg, 62%).

MS (ES+) 396

δH (d6 DMSO) 1.62-1.83 (6H, m), 2.03-2.15 (2H, m), 3.10-3.20 (1H, m), 7.06 (1H, s), 7.59 (1H, t), 7.77-7.85 (2H, m), 7.93-8.05 (2H, m), 8.30 (1H, d), 8.86 (1H, d), 12.23 (1H, br s), 14.15 (1H, br s).

A variety of other compounds of Formula I have been prepared by methods substantially similar to those described in Example 2. The characterization data for these compounds is summarized in Table 2 below and includes HPLC, LC/MS (observed) and 1H NMR data.

1H NMR data is summarized in Table 2 below wherein 1H NMR data was obtained at 400 MHz in deuterated DMSO, unless otherwise indicated, and was found to be consistent with structure.

TABLE 2

Characterization Data for Selected Compounds of Formula I

| Compound No I- | M + 1 (obs) | Rt (min) | ¹H-NMR |
|---|---|---|---|
| 1 | 384 | 8.17 | 0.83(2H, m), 1.00(2H, m), 2.00(1H, m), 6.10-6.51(2H, br s), 6.60(1H, d), 6.74((1H, m), 6.81(1H, s), 7.73(1H, t), 7.89(1H, d), 8.00(1H, t), 8.73(1H, d), 9.25(1H, d), 11.91(1H, br s), and 13.00(1H, br m) |
| 2 | 369 | 9.07 | 0.87(2H, m), 1.10(2H, m), 2.07(1H, m), 6.80(1H, s), 7.61(2H, m), 7.85(1H, t), 8.00(1H, t), 8.09(1H, t), 8.41(1H, d), 8.57(1H, d), and 9.41(1H, d) |
| 3 | 358 | 7.90 | 2.36(3H, s), 6.81(1H, s), 6.75(1H, dd), 7.03(1H, s), 7.71(1H, dd), 7.89(1H, d), 7.99(1H, dd), 8.85(1H, d), 9.29(1H, d), 12.17(1H, br s) and 13.53(1H, br s) |
| 6 | 405 | 9.78 | 7.47-7.62(4H, m), 7.80-7.90(2H, m), 7.91-8.12(5H, m), 8.30(1H, d), 9.33(1H, d) |
| 7 | 371 | 9.54 | 1.34(6H, d), 3.10(1H, m), 7.06(1H, s), 7.55-7.61(1H, m), 7.75-7.83(1H, m), 7.94-8.06(2H, m), 8.27(1H, d), 8.84(1H, d), 9.20(1H, d) |
| 8 | 395 | 9.38 | 6.72(1H, s), 7.15(1H, s), 7.54-7.70(2H, m), 7.82-7.91(3H, m), 8.00-8.12(2H, m), 8.30(1H, d), 8.91(1H, d), 12.45(1H, br s), 14.40(1H, br s) |
| 10 | 429 | 8.72 | 0.87-0.92(2H, m), 0.96-1.05(2H, m), 1.95-2.03(1H, m), 3.96(3H, s), 4.00(3H, s), 6.94(1H, s), 7.30(1H, s), 7.58(1H, s), 7.79(1H, t), 8.01(1H, t), 8.83(1H, d), 9.30(1H, d), 12.07(1H, br s), 14.05(1H, br s) |
| 11 | 457 | 9.50 | 1.50-1.90(6H, m), 2.00-2.20(2H, m), 3.10-3.20(1H, m), 3.90(3H, s), 4.00(3H, s), 7.00(1H, s), 7.20(1H, s), 7.65(1H, s), 7.85(1H, t), 8.10(1H, t), 8.85(1H, d), 9.35(1H, d) |
| 14 | 431 | 9.07 | 1.35(6H, d), 3.15(1H, m), 3.95(3H, s), 4.05(3H, s), 7.00(1H, s), 7.25(1H, s), 7.70(1H, s), 7.85(1H, t), 8.05(1H, t), 8.85(1H, d), 9.35(1H, d) |
| 16 | 456 | 9.01 | 0.86-0.91(2H, m), 1.03-1.10(2H, m), 1.32(3H, t), 2.00-2.07(1H, m), 4.25(2H, q), 6.95(1H, s), 7.48(1H, d), 7.80(1H, t), 8.05(1H, t), 8.10(1H, s), 8.19(1H, d), 8.86(1H, d), 9.25(1H, d), 10.59(1H, s), 12.18(1H, s), 13.74(1H, br s) |

Example 3

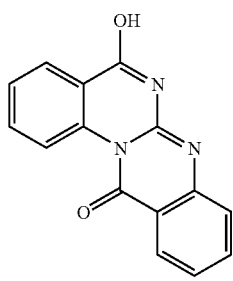

5-Hydroxy-quinazolino[3,2-a]quinazolin-12-one

To the 2-chloro-4-ethoxy-quinazoline (500 mg, 2.40 mmol) in a boiling tube was added methyl anthranilate (372 μL, 2.88 mmol). The mixture was heated with a hot air gun (approx. 400 deg C.) for 15 minutes before cooling to room temperature. The resulting crude product was suspended in ethyl acetate (10 mL) and heated to boiling. The mixture was then cooled and the pure off-white product isolated by filtration (257 mg).

MS (ES⁺) 263

δH (d⁶ DMSO) 7.39 (1H, t), 7.47 (1H, d), 7.59 (1H, t), 7.78 (1H, m), 7.81 (1H, m), 8.18 (2H, d), 9.17 (1H, d) and 12.33 (1H, br s).

Example 4

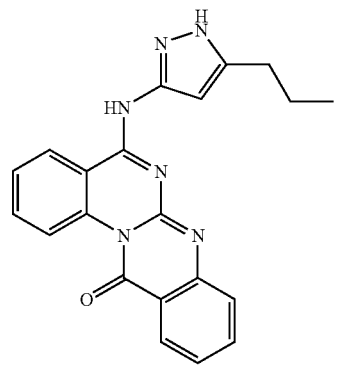

5-(5-Propyl-1H-pyrazol-3-ylamino)-quinazolino[3,2-a]quinazolin-12-one

The 5-hydroxy-quinazolino[3,2-a]quinazolin-12-one (72 mg, 0.27 mmol) was suspended in thionyl chloride (3 mL) and the mixture refluxed for 2 hours. The desired chloride intermediate was isolated by evaporation in vacuo.

The above was suspended in 1:1 THF/ⁱPrOH (3 mL) and treated with 5-propyl-1H-pyrazol-3-ylamine (68 mg, 0.54 mmol) and triethylamine (113 μL, 0.81 mmol). The mixture was stirred under a nitrogen atmosphere at 50 deg C. for 4 hours before concentrating in vacuo.

The above crude product was dissolved in DMSO/methanol and purified by preparative chromatography to yield the product as a TFA salt (46 mg).

MS (ES⁺) 371

δH (d⁶ DMSO) 0.95 (3H, t), 1.72 (2H, q), 2.69 (2H, m), 6.93 (1H, s), 7.58 (1H, m), 7.66 (1H, d), 7.80 (1H, m), 7.97 (1H, m), 8.05 (1H, m), 8.29 (1H, d), 8.80 (1H, d), 9.21 (1H, d), 12.12 (1H, br s), 12.75 (1H, br m) and 13.60 (1H, br m).

A variety of other compounds of Formula I have been prepared by methods substantially similar to those described in Example 4. The characterization data for these compounds is summarized in Table 3 below and includes HPLC, LC/MS (observed) and ¹H NMR data.

¹H NMR data is summarized in Table 3 below wherein ¹H NMR data was obtained at 400 MHz in deuterated DMSO, unless otherwise indicated, and was found to be consistent with structure.

TABLE 3

Characterization Data for Selected Compounds of Formula I

| Compound No I- | M + 1 (obs) | Rt (min) | $^1$H-NMR |
|---|---|---|---|
| 12 | 339 | 9.07 | 7.40(1H, t), 7.51(3H, m), 7.62(1H, d), 7.80(2H, d), 7.85(1H, t), 7.91(1H, t), 8.05(1H, t), 8.25(1H, d), 8.70(1H, d), 9.21(1H, d), 13.40(1H, br s) and 13.60(1H, br s) |
| 18 | 477 | 9.94 | 1.95(2H, t), 2.79(2H, m), 3.55(2H, t), 4.49(2H, s), 6.95(1H, s), 7.29(1H, m), 7.31(3H, m), 7.60(1H, t), 7.69(1H, d), 7.81(1H, t), 7.98(1H, t), 8.03(1H, t), 8.27(1H, d), 8.80(1H, d), 9.20(1H, d), 12.20(1H, br s), 12.80(1H, br s) and 13.31-13.85(1H, br s) |
| 19 | 386 | 7.75 | 1.95(2H, t), 2.78(2H, t), 2.89(2H, m), 6.94(1H, s), 7.56(1H, m), 7.65(1H, m), 7.71-7.86(4H, br s), 7.95(1H, m), 8.00(1H, m), 8.27(1H, d), 8.74(1H, s), 9.20(1H, d), 12.10(1H, s), 12.81(1H, s) and 13.60-14.0(1H, br s) |
| 20 | 387 | 8.24 | 1.89(2H, t), 2.76(2H, t), 3.50(2H, m), 6.96(1H, s), 7.59(1H, t), 7.66(1H, dd), 7.80(1H, t), 7.90-8.09(2H, br m), 8.28(1H, d), 8.80(1H, d), 9.20(1H, d), 12.20(1H, br s), 12.85(1H, s) and 13.35-13.80(1H, br s) |
| 21 | 401 | 8.88 | — |

Example 5

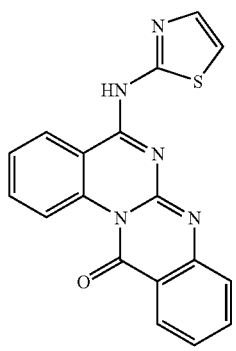

5-(Thiazol-2-ylamino)-quinazolino[3,2-a]quinazolin-12-one

A pressure tube was charged with 5-chloro-quinazolino[3,2-a]quinazolin-12-one (200 mg, 0.71 mmol), Pd$_2$(dba)$_3$ (25 mg, 0.028 mmol), Xantphos (25 mg, 0.043 mmol), 2-aminothiazole (71 mg, 0.85 mmol), Na$_2$CO$_3$ (fine powder, 71 mg, 0.85 mmol) and anhydrous dioxane/toluene (1:1, 5 mL). The mixture was stirred with heating at 100 deg C. for 17 hours. After this period the mixture was cooled, concentrated in vacuo and purified by preparative chromatography, to yield the desired product (TFA salt) as a yellow powder (130 mg).

MS (ES$^+$) 346, (ES$^-$) 344

δH (d$^6$ DMSO) 7.51 (1H, t), 7.68 (1H, m), 7.71 (2H, m), 7.85 (1H, m), 7.95 (2H, m), 8.24 (1H, d), 8.58 (1H, d), 9.28 (1H, d) and 13.40-14.00 (1H, br s)

A variety of other compounds of Formula I have been prepared by methods substantially similar to those described in Example 5. The characterization data for these compounds is summarized in Table 4 below and includes HPLC, LC/MS (observed) and $^1$H NMR data.

$^1$H NMR data is summarized in Table 4 below wherein $^1$H NMR data was obtained at 400 MHz in deuterated DMSO, unless otherwise indicated, and was found to be consistent with structure.

TABLE 4

Characterization Data for Selected Compounds of Formula I

| Compound No I- | M + 1 (obs) | Rt (min) | $^1$H-NMR |
|---|---|---|---|
| 23 | 340 | 9.47 | 7.25(1H, t), 7.42(1H, t), 7.61(2H, t), 7.82(2H, m), 7.97(1H, t), 8.21(1H, dd), 8.52(1H, d), 8.64(1H, d) and 9.25(1H, d). |
| 24 | 378 | 10.34 | 7.19(1H, t), 7.50(1H, t), 7.60(2H, d), 7.67(1H, d)), 7.81(1H, m), 7.90(2H, m), 8.13(1H, m), 8.29(1H, d), 8.85(1H, m), 9.31(1H, d), 12.21(1H, m), 13.31(1H, m) and 13.36-132.70(1H, br m) |

Example 6

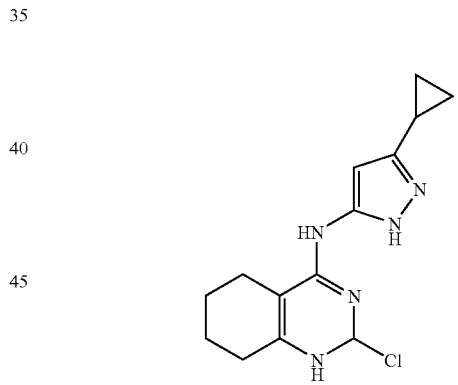

(2-Chloro-1,2,5,6,7,8-hexahydro-quinazolin-4-yl)-(5-cyclopropyl-2H-pyrazol-3-yl)-amine 2,4-Dichloro-1,2,5,6,7,8-hexahydro-quinazoline (1 g, 4.93 mmol) and 3-amino-5-cyclopropylpyrazole (0.606 g, 4.93 mmol) in ethanol (8 ml) was treated with triethylamine (1.24 ml, 8.87 mmol) and the mixture heated at 120° C. for 3 days, cooled and filtered to give (0.72 g, 51%) as a colourless solid.

MS (ES$^+$) 286

δH (d$^6$ DMSO) 0.60-0.65 (2H, m), 0.80-0.90 (2H, m), 1.62-1.70 (4H, m), 1.80-1.87 (1H, m), 2.30-2.32 (2H, m), 2.52-2.56 (2H, m), 6.15 (1H, s), 8.99 (1H, s).

Example 7

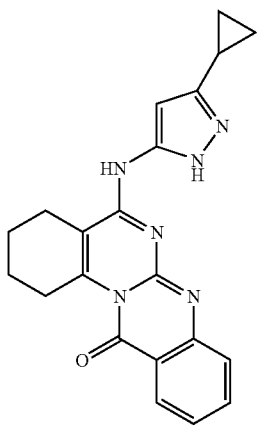

5-(5-Cyclopropyl-2H-pyrazol-3-ylamino)-1,2,3,4-tetrahydro-quinazolino[3,2-a]quinazolin-12-one (2-Chloro-1,2,5,6,7,8-hexahydro-quinazolin-4-yl)-(5-cyclopropyl-2H-pyrazol-3-yl)-amine (150 mg, 0.518 mmol), in methyl anthranilate (0.1 ml, 0.777 mmol) was heated to 135° C. for 4 hours to give a brown gum. This was dissolved in methanol/dichloromethane and added to a mixture of ethyl acetate and aqueous sodium bicarbonate. The mixture was extracted with ethyl acetate and the extracts dried over magnesium sulphate and concentrated. Purification by flash chromatography on silica gel eluting with 4% methanol/dichloromethane gave a pale yellow gum. This was dissolved in 0.5M HCl in methanol and crystallised by the dropwise addition of diethyl ether to give cream coloured crystals of 5-(5-cyclopropyl-2H-pyrazol-3-ylamino)-1,2,3,4-tetrahydro-quinazolino[3,2-a]quinazolin-12-one hydrochloride (15 mg, 7%).

MS (ES+) 372

$\delta$H (d$^6$ DMSO) 0.78-0.89 (2H, m), 0.96-1.03 (2H, m), 1.64-1.74 (2H, m), 1.78-1.85 (2H, m), 1.94-2.02 (1H, m), 2.65-2.74 (2H, m), 3.19-3.28 (2H, m), 6.71 (1H, s), 7.51 (1H, t), 7.72 (1H, d), 7.94 (1H, t), 8.14 (1H, d), 10.73 (1H, s), 11.58 (1H, br s).

A variety of other compounds of Formula I have been prepared by methods substantially similar to those described in Example 7. The characterization data for these compounds is summarized in Table 5 below and includes HPLC, LC/MS (observed) and $^1$H NMR data.

$^1$H NMR data is summarized in Table 5 below wherein $^1$H NMR data was obtained at 400 MHz in deuterated DMSO, unless otherwise indicated, and was found to be consistent with structure.

TABLE 5

Characterization Data for Selected Compounds of Formula I

| Compound No I- | M + 1 (obs) | Rt (min) | $^1$H-NMR |
|---|---|---|---|
| 4 | 334 | 7.23 | 0.88(2H, m), 1.00(2H, m), 1.99(1H, m), 6.13(1H, s), 6.45(1H, s), 6.57(1H, dd), 6.68(1H, d), 7.69(1H, d) and 8.71(1H, d) |
| 5 | 333 | 8.78 | 0.85(2H, m), 1.00(2H, m), 2.03(1H, m), 6.21(1H, s), 6.63(1H, s), 7.31(1H, t), 7.45(1H, dd), 7.76(1H, t), 8.05(1H, d), 11.05(1H br s) and 11.02(1H, br s) |

TABLE 5-continued

Characterization Data for Selected Compounds of Formula I

| Compound No I- | M + 1 (obs) | Rt (min) | $^1$H-NMR |
|---|---|---|---|
| 15 | 359 | 8.82 | 0.75(2H, m), 1.00(2H, m), 2.00(1H, m), 2.15(2H, m), 2.80(2H, m), 3.75(2H, m), 6.75(2H, m), 7.35(2H, m), 7.55(1H, d), 7.75(1H, t), 8.05(1H, d), 9.95(1H, m) |

Example 8

ITK Inhibition Assay (Radioactive)

Compounds were screened for their ability to inhibit Itk using a radioactive-phosphate incorporation assay. Assays were carried out in a mixture of 100 mM HEPES (pH 7.5), 10 mM MgCl$_2$, 25 mM NaCl, 0.01% BSA and 1 mM DTT. Final substrate concentrations were 15 µM [γ-33P]ATP (400 mCi 33P ATP/mmol ATP, Amersham Pharmacia Biotech/Sigma Chemicals) and 2 µM peptide (SAM68 protein D332-443). Assays were carried out at 25° C. in the presence of 30 nM Itk. An assay stock buffer solution was prepared containing all of the reagents listed above, with the exception of ATP and the test compound of interest. 50 µL of the stock solution was placed in a 96 well plate followed by addition of 1.5 µL of DMSO stock containing serial dilutions of the test compound (typically starting from a final concentration of 15 µM with 2-fold serial dilutions) in duplicate (final DMSO concentration 1.5%). The plate was pre-incubated for 10 minutes at 25° C. and the reaction initiated by addition of 50 µL [γ-33P]ATP (final concentration 15 µM).

The reaction was stopped after 10 minutes by the addition of 50 µL of a TCA/ATP mixture (20% TCA, 0.4 mM ATP). A Unifilter GF/C 96 well plate (Perkin Elmer Life Sciences, Cat no. 6005174) was pretreated with 50 µL Milli Q water prior to the addition of the entire reaction mixture (150 µL). The plate was washed with 200 µL Milli Q water followed by 200 mL of a TCA/ATP mixture (5% TCA, 1 mM ATP). This wash cycle was repeated a further 2 times. After drying, 30 µL Optiphase 'SuperMix' liquid scintillation cocktail (Perkin Elmer) was added to the well prior to scintillation counting (1450 Microbeta Liquid Scintillation Counter, Wallac).

IC50 data were calculated from non-linear regression analysis of the initial rate data using the Prism software package (GraphPad Prism version 3.0cx for Macintosh, GraphPad Software, San Diego Calif., USA).

Assays were carried out in a mixture of 20 mM MOPS (pH 7.0), 10 mM MgCl$_2$, 0.1% BSA and 1 mM DTT. Final substrate concentrations in the assay were 7.5 µM [γ-33P]ATP (400 mCi 33P ATP/mmol ATP, Amersham Pharmacia Biotech/Sigma Chemicals) and 3 µM peptide (SAM68 protein D332-443). Assays were carried out at 25° C. in the presence of 50 nM Itk. An assay stock buffer solution was prepared containing all of the reagents listed above, with the exception of ATP and the test compound of interest. 50 µL of the stock solution was placed in a 96 well plate followed by addition of 2 µL of DMSO stock containing serial dilutions of the test compound (typically starting from a final concentration of 50 µM with 2-fold serial dilutions) in duplicate (final DMSO concentration 2%). The plate was pre-incubated for 10 minutes at 25° C. and the reaction initiated by addition of 50 µL [γ-33P]ATP (final concentration 7.5 µM).

The reaction was stopped after 10 minutes by the addition of 100 mL 0.2M phosphoric acid+0.01% TWEEN 20. A multiscreen phosphocellulose filter 96-well plate (Millipore, Cat no. MAPHNOB50) was pretreated with 100 μL 0.2M phosphoric acid+0.01% TWEEN 20 prior to the addition of 170 mL of the stopped assay mixture. The plate was washed with 4×200 μL 0.2M phosphoric acid+0.01% TWEEN 20. After drying, 30 μL Optiphase 'SuperMix' liquid scintillation cocktail (Perkin Elmer) was added to the well prior to scintillation counting (1450 Microbeta Liquid Scintillation Counter, Wallac).

Ki(app) data were calculated from non-linear regression analysis of the initial rate data using the Prism software package (GraphPad Prism version 3.0cx for Macintosh, GraphPad Software, San Diego Calif., USA).

Example 9

ITK Inhibition Assay (AlphaScreen™)

Compounds were screened for their ability to inhibit Itk using an AlphaScreen™ phosphotyrosine assay at Vertex Pharmaceuticals. Assays were carried out in a mixture of 20 mM MOPS (pH 7.0), 10 mM $MgCl_2$, 0.1% BSA and 1 mM DTT. Final substrate concentrations in the assay were 100 μM ATP (Sigma Chemicals) and 2 μM peptide (Biotinylated SAM68 Δ332-443). Assays were carried out at 25° C. and in the presence of Itk (30 nM). An assay stock buffer solution was prepared containing all of the reagents listed above, with the exception of ATP and the test compound of interest. 25 μL of the stock solution was placed in each well of a 96 well plate followed by 1 μL of DMSO containing serial dilutions of the test compound (typically starting from a final concentration of 15 μM) in duplicate (final DMSO concentration 2%). The plate was preincubated for 10 minutes at 25° C. and the reaction initiated by addition of 25 μL ATP (final concentration 100 μM). Background counts were determined by the addition of 5 μL 500 mM EDTA to control wells containing assay stock buffer and DMSO prior to initiation with ATP.

The reaction was stopped after 30 minutes by diluting the reaction 225-fold into MOPS buffer (20 mM MOPS (pH 7.0), 1 mM DTT, 10 mM $MgCl_2$, 0.1% BSA) containing 50 mM EDTA to bring the final concentration of Biotin-SAM68 to 9 nM.

AlphaScreen™ reagents were prepared according to the manufacturers instructions (AlphaScreen™ phosphotyrosine (P-Tyr-100) assay kit, PerkinElmer catalogue number 6760620C). Under subdued lighting, 20 μL of AlphaScreen™ reagents were placed in each well of a white half area 96 well plate (Corning Inc.—COSTAR 3693) with 30 μL of the stopped, diluted kinase reactions. Plates were incubated in the dark for 60 minutes prior to reading on a Fusion Alpha plate reader (PerkinElmer).

After removing mean background values for all of the data points, Ki(app) data were calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of Itk. Preferred compounds show Ki below 1 μM in the AlphaScreen™ assay (I-1, I-2, I-3, I-7, I-9, I-10, I-11, I-13, I-14, I-15, I-16, I-17, I-20, I-21).

Example 10

BTK Inhibition Assay (Radioactive)

Compounds were screened for their ability to inhibit Btk using a radioactive-phosphate incorporation assay at Vertex Pharmaceuticals. Assays were carried out in a mixture of 20 mM MOPS (pH 7.0), 10 mM $MgCl_2$, 0.1% BSA and 1 mM DTT. Final substrate concentrations in the assay were 50 μM [γ-33P]ATP (200 mCi 33P ATP/mmol ATP, Amersham Pharmacia Biotech, Amersham, UK/Sigma Chemicals) and 2 μM peptide (SAM68 D332-443). Assays were carried out at 25° C. and in the presence of 25 nM Btk. An assay stock buffer solution was prepared containing all of the reagents listed above, with the exception of the peptide and the test compound of interest. 75 μL of the stock solution was placed in a 96 well plate followed by addition of 2 μL of DMSO stock containing serial dilutions of the test compound (typically starting from a final concentration of 15 μM) in duplicate (final DMSO concentration 2%). The plate was preincubated for 15 minutes at 25° C. and the reaction initiated by addition of 25 μL peptide (final concentration 2 μM). Background counts were determined by the addition of 100 mL 0.2M phosphoric acid+0.01% TWEEN to control wells containing assay stock buffer and DMSO prior to initiation with peptide.

The reaction was stopped after 10 minutes by the addition of 100 mL 0.2M phosphoric acid+0.01% TWEEN. A multi-screen phosphocellulose filter 96-well plate (Millipore, Cat no. MAPHN0B50) was pretreated with 100 μL 0.2M phosphoric acid+0.01% TWEEN 20 prior to the addition of 170 mL of the stopped assay mixture. The plate was washed with 4×200 μL 0.2M phosphoric acid+0.01% TWEEN 20. After drying, 30 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis using the Prism software package (GraphPad Prism version 3.0cx for Macintosh, GraphPad Software, San Diego Calif., USA).

Example 11

BTK Inhibition Assay (AlphaScreen™)

Compounds were screened for their ability to inhibit Btk using an AlphaScreen™ phosphotyrosine assay at Vertex Pharmaceuticals. Assays were carried out in a mixture of 20 mM MOPS (pH 7.0), 10 mM $MgCl_2$, 0.1% BSA and 1 mM DTT. Final substrate concentrations in the assay were 50 μM ATP (Sigma Chemicals) and 2 μM peptide (Biotinylated SAM68 D332-443). Assays were carried out at 25° C. and in the presence of 25 nM Btk. An assay stock buffer solution was prepared containing all of the reagents listed above, with the exception of peptide and the test compound of interest. 37.5 μL of the stock solution was placed in each well of a 96 well plate followed by 1 μL of DMSO containing serial dilutions of the test compound (typically starting from a final concentration of 15 μM) in duplicate (final DMSO concentration 2%). The plate was preincubated for 15 minutes at 25° C. and the reaction initiated by addition of 12.5 μL peptide (final concentration 2 μM). Background counts were determined by the addition of 5 μL 500 mM EDTA to control wells containing assay stock buffer and DMSO prior to initiation with Biotin-SAM68.

The reaction was stopped after 30 minutes by diluting the reaction 225-fold into MOPS buffer (20 mM MOPS (pH 7.0), 1 mM DTT, 10 mM $MgCl_2$, 0.1% BSA) containing 50 mM EDTA to bring the final concentration of peptide to 9 nM.

AlphaScreen™ reagents were prepared according to the manufacturers instructions (AlphaScreen™ phosphotyrosine (P-Tyr-100) assay kit, PerkinElmer catalogue number 6760620C). Under subdued lighting, 20 µL of AlphaScreen™ reagents were placed in each well of a white half area 96 well plate (Corning Inc.—COSTAR 3693) with 30 µL of the stopped, diluted kinase reactions. Plates were incubated in the dark for 60 minutes prior to reading on a Fusion Alpha plate reader (PerkinElmer).

After removing mean background values for all of the data points, Ki(app) data were calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of Btk.

Example 12

RLK Inhibition Assay (UV)

Compounds were screened for their ability to inhibit Rlk using a standard coupled enzyme assay (Fox et al., *Protein Sci.,* (1998) 7, 2249). Assays were carried out in a mixture of 20 mM MOPS (pH 7.0), 10 mM MgCl$_2$, 0.1% BSA and 1 mM DTT. Final substrate concentrations in the assay were 100 µM ATP (Sigma Chemicals) and 10 µM peptide (Poly Glu:Tyr 4:1). Assays were carried out at 30° C. and in the presence of 40 nM Rlk. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of RLK.

The invention claimed is:
1. A compound of formula (I):

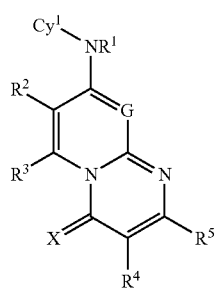

(I)

or a pharmaceutically acceptable salt thereof,
wherein R$^1$ is —QR$^X$; wherein Q is a bond or is a C$_1$-C$_6$ alkylidene chain wherein up to two methylene units of Q are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and R$^X$ is R', halogen, NO$_2$, or CN; with the requirement that R1 must be either bound via an R1 carbon atom or must be H;

each occurrence of R is independently selected from hydrogen or an optionally substituted C$_{1-8}$ aliphatic group wherein if said aliphatic group contains one or more units of unsaturation, said aliphatic group is a C$_2$-C$_8$ aliphatic chain, and wherein if said aliphatic group is a cycloaliphatic group, said cycloaliphatic group is a C$_3$-C$_8$ cycloaliphatic group; and R' is selected from hydrogen or an optionally substituted group selected from C$_{1-8}$ aliphatic, C$_6$-C$_{10}$ aryl, a heteroaryl ring having 5-10 ring atoms, or a heterocyclyl ring having 3-10 ring atoms, or wherein R and R' taken together with the atom(s) to which they are bound, or two occurrences of R taken together with the atom(s) to which they are bound, form an optionally substituted group selected from a 3-10 membered cycloalkyl ring, a C$_6$-C$_{10}$aryl ring, a heteroaryl ring having 5-10 ring atoms, or a heterocyclyl ring having 3-10 ring atoms;

Cy$^1$ is a 5-7-membered monocyclic aryl ring or an 8-10-membered bicyclic aryl ring having 0-3 heteroatoms independently selected from nitrogen, oxygen, or sulfur, or is a 3-8-membered saturated or partially unsaturated monocyclic ring having 0-3 heteroatoms independently selected from nitrogen, oxygen, or sulfur, wherein Cy$^1$ is optionally substituted with y occurrences of —YR$^Y$, wherein y is 0-5, Y is a bond or is a C$_1$-C$_6$ alkylidene chain wherein up to two methylene units of Y are optionally and independently replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO$_2$NR—, —NRSO$_2$—, —NRSO$_2$NR—, and each occurrence of R$^Y$ is independently R', halogen, NO$_2$, or CN;

R$^2$ and R$^3$, taken together, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein the ring formed by R$^2$ and R$^3$ taken together is optionally substituted at one or more carbon or nitrogen atoms with m independent occurrences of —WR$^W$, R$^4$ and R$^5$, taken together, form an optionally substituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur, wherein the ring formed by R$^4$ and R$^5$, taken together is optionally substituted at one or more carbon or nitrogen atoms with n independent occurrences of Z—R$^Z$; m and n are each independently 0-5;

W and Z are each independently a bond or is an optionally substituted C$_1$-C$_6$ alkylidene chain wherein up to two methylene units of W or Z are optionally replaced by —CO—, —CS—, —COCO—, —CONR—, —CONRNR—, —CO$_2$—, —OCO—, —NRCO$_2$—, —O—, —NRCONR—, —OCONR—, —NRNR, —NRNRCO—, —NRCO—, —S—, —SO, —SO$_2$—, —NR—, —SO₂NR—, —NRSO₂—, —NRSO₂NR—, and each occurrence of $R^W$ and $R^Z$ is independently R', halogen, NO₂, or CN;

X is O, S, or $[C(R^1)_2]_q$, where q is 1 or 2; and

G is N or $CR^6$, wherein $R^6$ is halogen, CN, NO₂, or $QR^X$, wherein the heteroatoms of a heterocyclyl or heteroaryl ring are selected from oxygen, sulfur, or nitrogen;

optional substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH₂)₁₋₂(Ph), optionally substituted with R°; —CH=CH(Ph), optionally substituted with R°; —NO₂; —CN; —N(R°)₂; —NR°C(O)R°; —NR°C(S)R°; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; or —(CH₂)₀₋₂NHC(O)R° wherein each independent occurrence of R° is selected from hydrogen, optionally substituted C₁₋₆ aliphatic, an unsubstituted 5-6 membered heteroaryl or heterocyclic ring, phenyl, —O(Ph), or —CH₂(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur Optional substituents on the aliphatic group of R° are selected from NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), O(haloC₁₋₄ aliphatic), or haloC₁₋₄aliphatic, wherein each of the foregoing C₁₋₄aliphatic groups of R° is unsubstituted;

optional substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted C₁₋₆ aliphatic;

optional substituents on the aliphatic group of R* are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄aliphatic groups of R* is unsubstituted; and optional substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 5-8-membered heterocyclyl, aryl, or heteroaryl ring or a 3-8-membered cycloalkyl ring having 0-3 heteroatoms independently selected from nitrogen, oxygen, or sulfur;

optional substituents on the aliphatic group or the phenyl ring of R⁺ are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄aliphatic groups of R⁺ is unsubstituted;

provided that:

when X is O; $R^1$ is hydrogen; $R^2$ and $R^3$, taken together are unsubstituted phenyl; $R^4$ and $R^5$, taken together are unsubstituted phenyl; and G is N; then $Cy^1$ is not unsubstituted phenyl.

2. The compound of claim 1, wherein $R^1$ is hydrogen, —COR', CONRR', or is an optionally substituted C₁-C₆ alkyl group.

3. The compound of claim 1, wherein $R^1$ is hydrogen.

4. The compound of any one of claims 1-3, wherein $Cy^1$ is a group selected from:

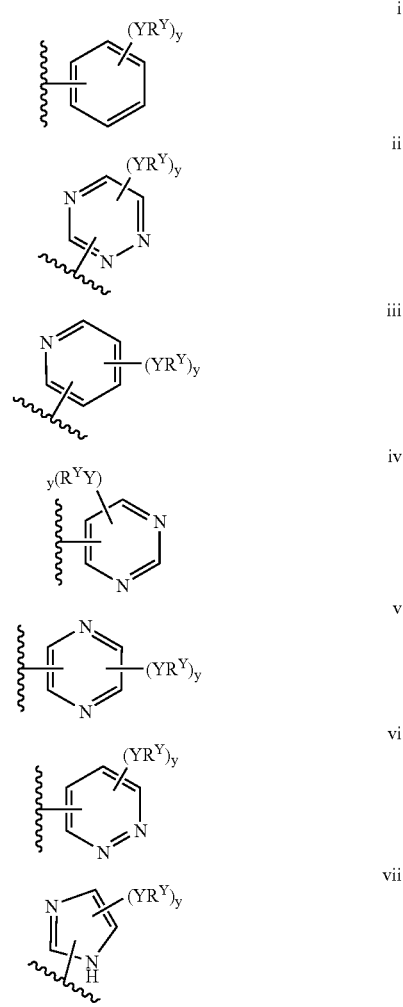

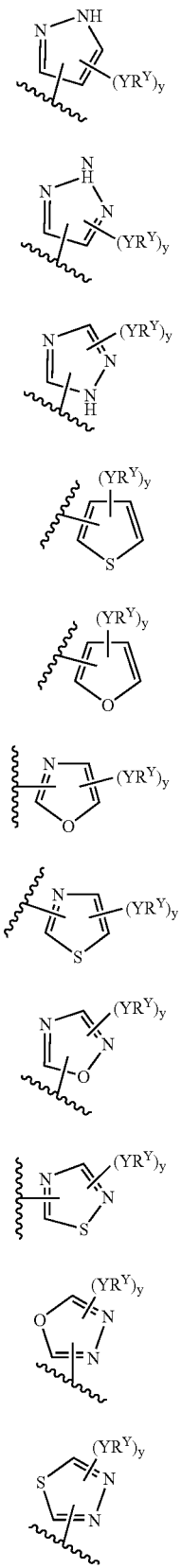

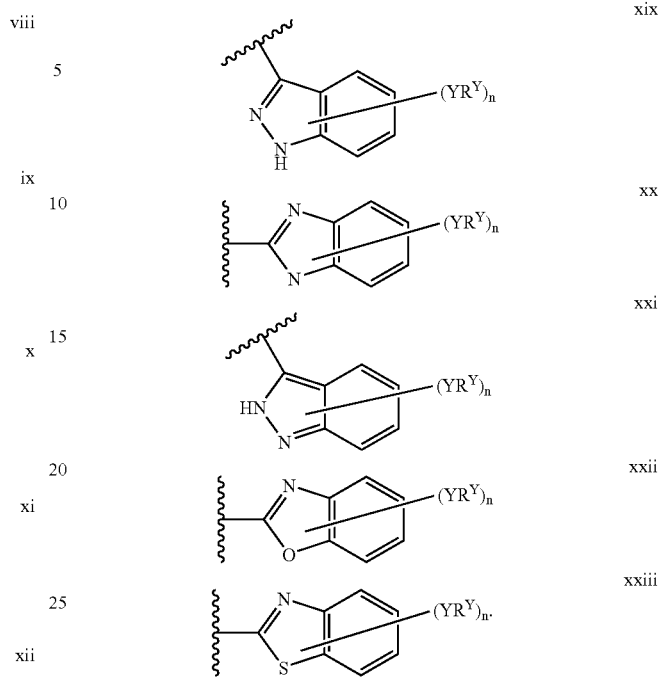

5. The compound of claim 3, wherein $Cy^1$ is phenyl (i), pyridyl (iii), pyrimidinyl (iv), imidazolyl (vi), pyrazolyl (vii), triazolyl (x), thiazolyl (xiv), or indazolyl (xix) or (xxi).

6. The compound of claim 5, wherein $Cy^1$ is pyrazolyl (vii).

7. The compound of claim 6, wherein each occurrence of —$YR^Y$, when present, is independently halogen, R', CN, $NO_2$, —$N(R')_2$, —$CH_2N(R')_2$, —$(CH_2)_2N(R')_2$, —$(CH_2)_3N(R')_2$, —OR', —$CH_2OR'$, —$(CH_2)_2OR'$, —$(CH_2)_3OR'$, —SR', —$CH_2SR'$, —$(CH_2)_2SR'$, —$(CH_2)_3SR'$, —COOR', —NRCOR', NRCOOR', —$CON(R')_2$, or —$S(O)_2N(R')_2$.

8. The compound of claim 6, wherein —$YR^Y$ groups are each independently F, Cl, Br, I, —CN, —COOMe, —COOH, —OH, $NH_2$, SH, —$SO_2NH_2$, —$CON(CH_3)_2$, —$O(C_1$-$C_6alkyl)$, —$CH_2O(C_1$-$C_6alkyl)$, —$(CH_2)_2O(C_1$-$C_6alkyl)$, —$(CH_2)_3O(C_1$-$C_6alkyl)$, —$S(C_1$-$C_6alkyl)$, —$CH_2S(C_1$-$C_6alkyl)$, —$(CH_2)_2S(C_1$-$C_6alkyl)$, —$(CH_2)_3S(C_1$-$C_6alkyl)$, —$N(C_1$-$C_6alkyl)_2$, —$CH_2N(C_1$-$C_6alkyl)_2$, —$(CH_2)_2N(C_1$-$C_6alkyl)_2$, —$(CH_2)_3N(C_1$-$C_6alkyl)_2$, wherein each $C_1$-$C_6alkyl$ group is optionally substituted with R', —OR', —$N(R')_2$, —SR', —$SO_2N(R')_2$, —$NRSO_2R'$, —$CON(R')_2$, or —NRCOR', or —$YR^Y$ groups are each independently an optionally substituted group selected from $C_1$-$C_6alkyl$, $C_3$-$C_8cycloalkyl$, phenyl, phenyloxy, benzyl, benzyloxy, pyridyl, pyrimidinyl, thienyl, N-morpholinyl, N-piperidinyl, N-piperazinyl, or furanyl.

9. The compound of claim 4, wherein $R^2$ and $R^3$, taken together with the atoms to which they are bound, form an unsubstituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur.

10. The compound of claim 4, wherein $R^2$ and $R^3$, taken together with the carbon atoms to which they are bound form an optionally substituted ring selected from one of the following groups:

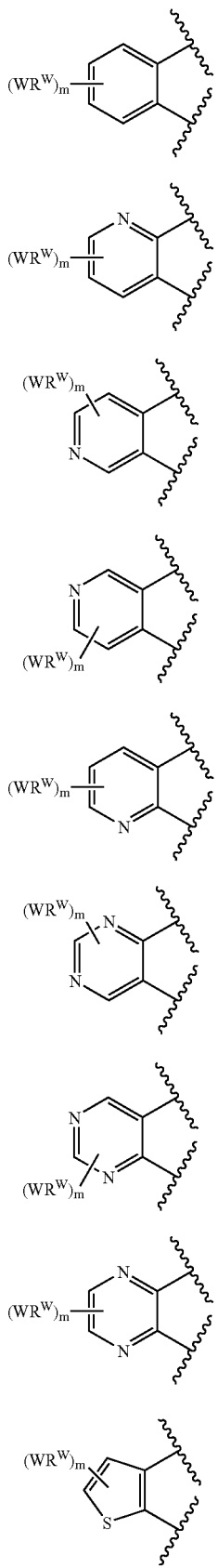
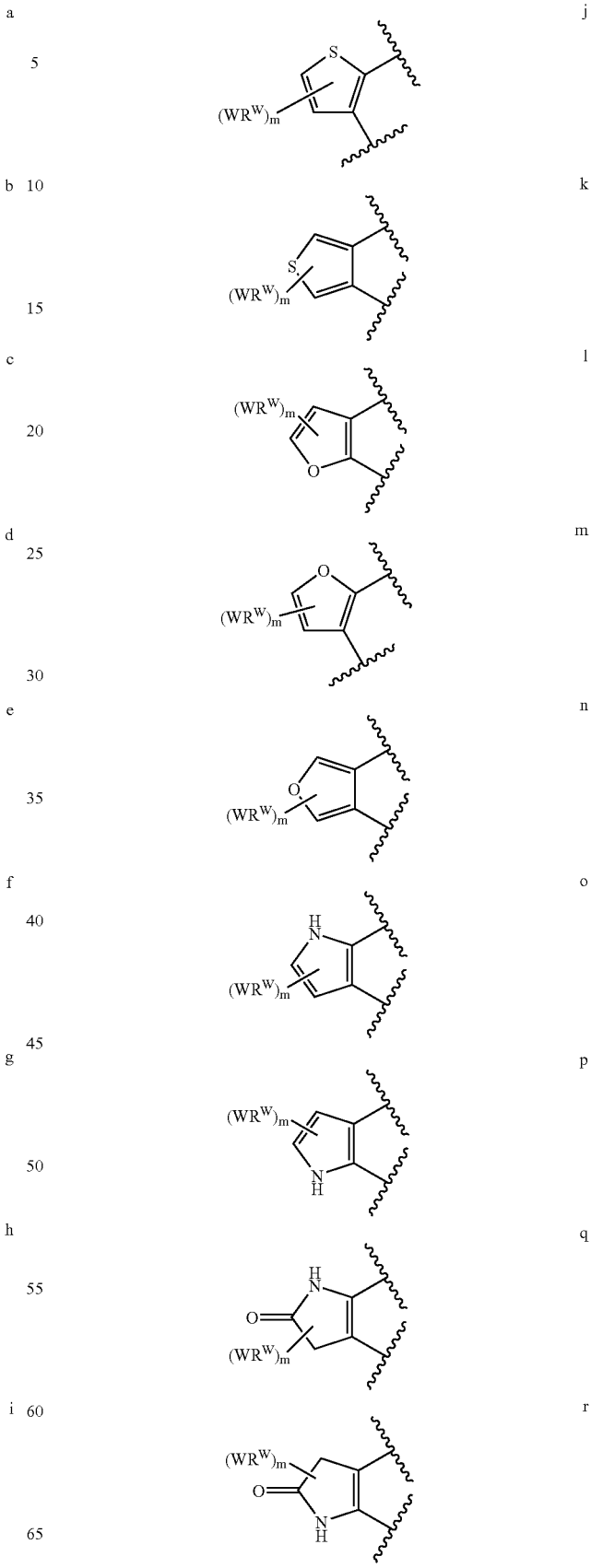

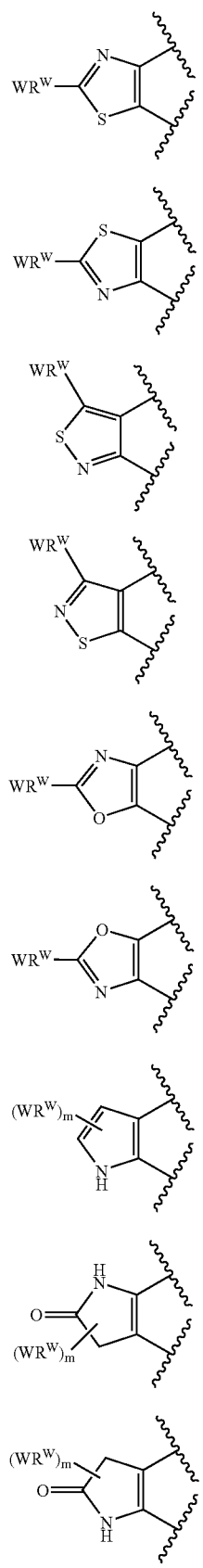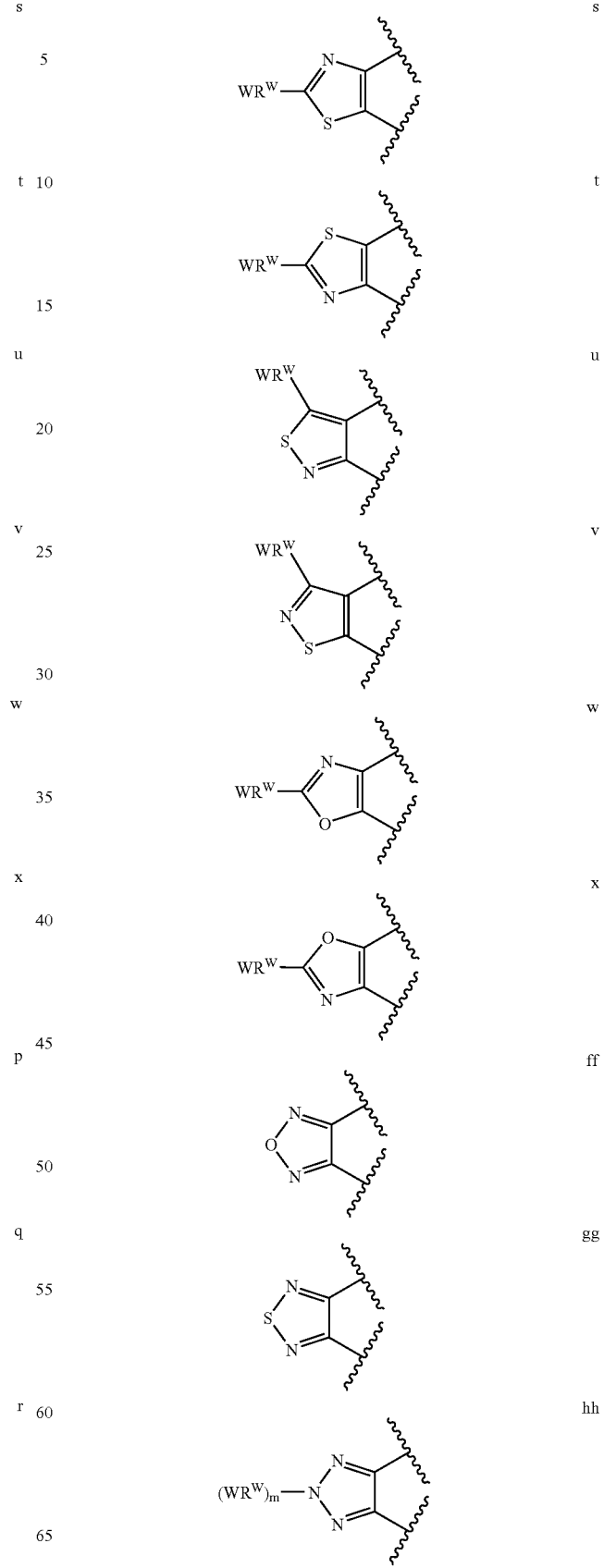

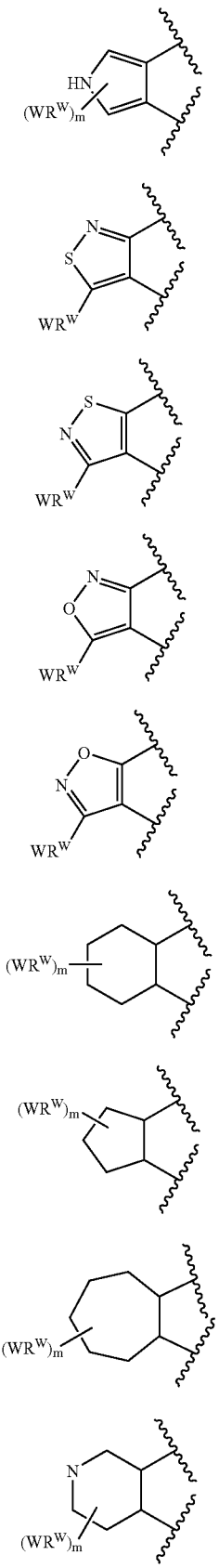
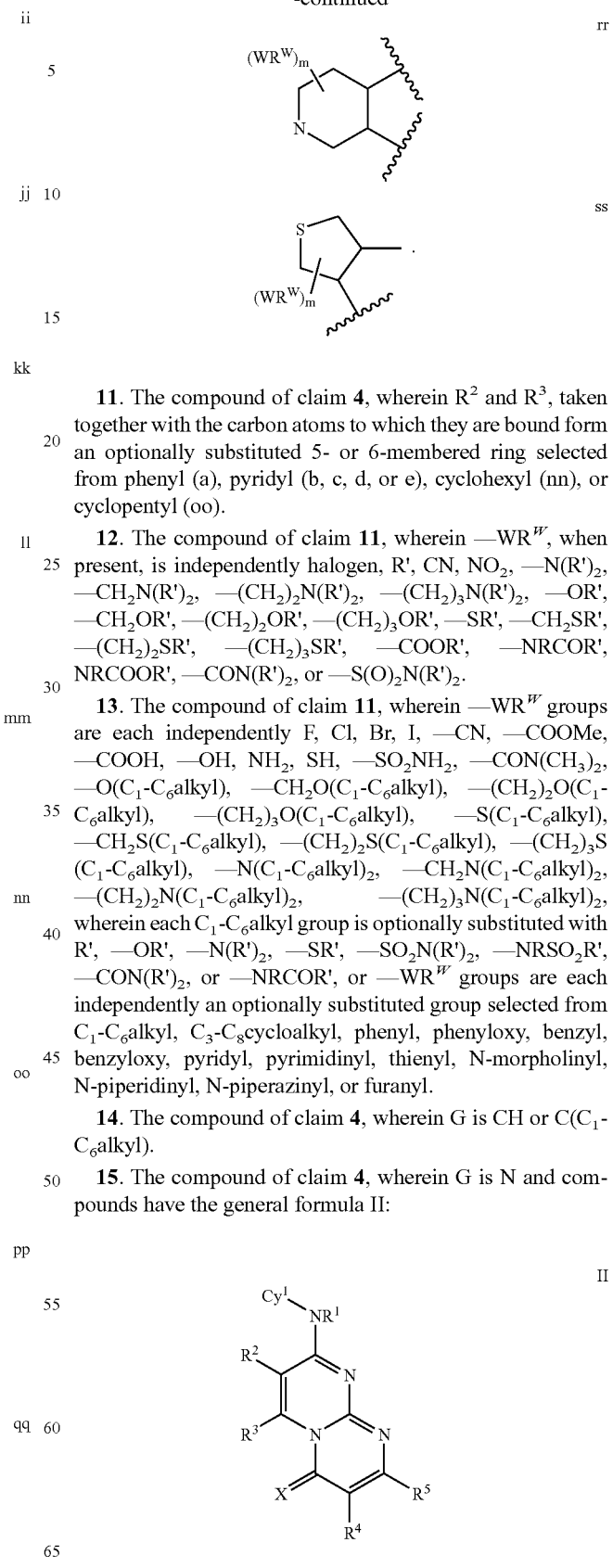

11. The compound of claim 4, wherein $R^2$ and $R^3$, taken together with the carbon atoms to which they are bound form an optionally substituted 5- or 6-membered ring selected from phenyl (a), pyridyl (b, c, d, or e), cyclohexyl (nn), or cyclopentyl (oo).

12. The compound of claim 11, wherein —WR$^W$, when present, is independently halogen, R', CN, NO$_2$, —N(R')$_2$, —CH$_2$N(R')$_2$, —(CH$_2$)$_2$N(R')$_2$, —(CH$_2$)$_3$N(R')$_2$, —OR', —CH$_2$OR', —(CH$_2$)$_2$OR', —(CH$_2$)$_3$OR', —SR', —CH$_2$SR', —(CH$_2$)$_2$SR', —(CH$_2$)$_3$SR', —COOR', —NRCOR', NRCOOR', —CON(R')$_2$, or —S(O)$_2$N(R')$_2$.

13. The compound of claim 11, wherein —WR$^W$ groups are each independently F, Cl, Br, I, —CN, —COOMe, —COOH, —OH, NH$_2$, SH, —SO$_2$NH$_2$, —CON(CH$_3$)$_2$, —O(C$_1$-C$_6$alkyl), —CH$_2$O(C$_1$-C$_6$alkyl), —(CH$_2$)$_2$O(C$_1$-C$_6$alkyl), —(CH$_2$)$_3$O(C$_1$-C$_6$alkyl), —S(C$_1$-C$_6$alkyl), —CH$_2$S(C$_1$-C$_6$alkyl), —(CH$_2$)$_2$S(C$_1$-C$_6$alkyl), —(CH$_2$)$_3$S(C$_1$-C$_6$alkyl), —N(C$_1$-C$_6$alkyl)$_2$, —CH$_2$N(C$_1$-C$_6$alkyl)$_2$, —(CH$_2$)$_2$N(C$_1$-C$_6$alkyl)$_2$, —(CH$_2$)$_3$N(C$_1$-C$_6$alkyl)$_2$, wherein each C$_1$-C$_6$alkyl group is optionally substituted with R', —OR', —N(R')$_2$, —SR', —SO$_2$N(R')$_2$, —NRSO$_2$R', —CON(R')$_2$, or —NRCOR', or —WR$^W$ groups are each independently an optionally substituted group selected from C$_1$-C$_6$alkyl, C$_3$-C$_8$cycloalkyl, phenyl, phenyloxy, benzyl, benzyloxy, pyridyl, pyrimidinyl, thienyl, N-morpholinyl, N-piperidinyl, N-piperazinyl, or furanyl.

14. The compound of claim 4, wherein G is CH or C(C$_1$-C$_6$alkyl).

15. The compound of claim 4, wherein G is N and compounds have the general formula II:

or a pharmaceutically acceptable salt thereof.

16. The compound of claim 4, wherein X is O and compounds have the general formula III:

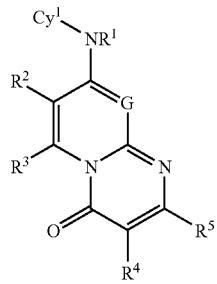

III or a pharmaceutically acceptable salt thereof.

17. The compound of claim 4, wherein X is O and G is N and compounds have the general formula IV:

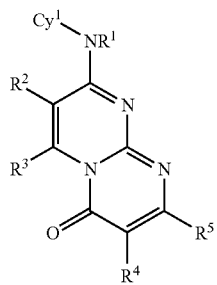

IV or a pharmaceutically acceptable salt thereof.

18. The compound of claim 4, wherein $R^4$ and $R^5$, taken together with the atoms to which they are bound, form an unsubstituted 5-, 6-, or 7-membered monocyclic aryl ring having 0-3 heteroatoms independently selected from nitrogen, oxygen, or sulfur or a 5-, 6-, or 7-membered saturated or partially unsaturated monocyclic ring having 0-3 heteroatoms independently selected from nitrogen, oxygen, or sulfur.

19. The compound of claim 4, wherein $R^4$ and $R^5$, taken together with the carbon atoms to which they are bound form an optionally substituted ring selected from one of the following groups:

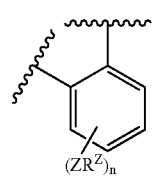

a-i

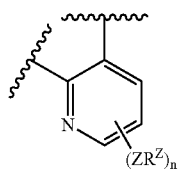

b-i

-continued

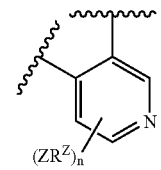

c-i

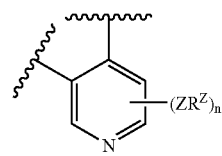

d-i

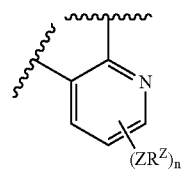

e-i

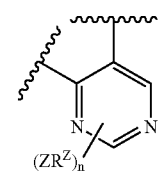

f-i

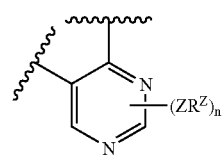

g-i

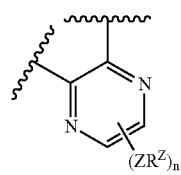

h-i

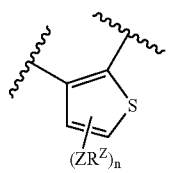

i-i

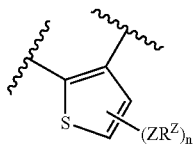

j-i

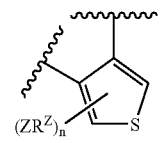

k-i

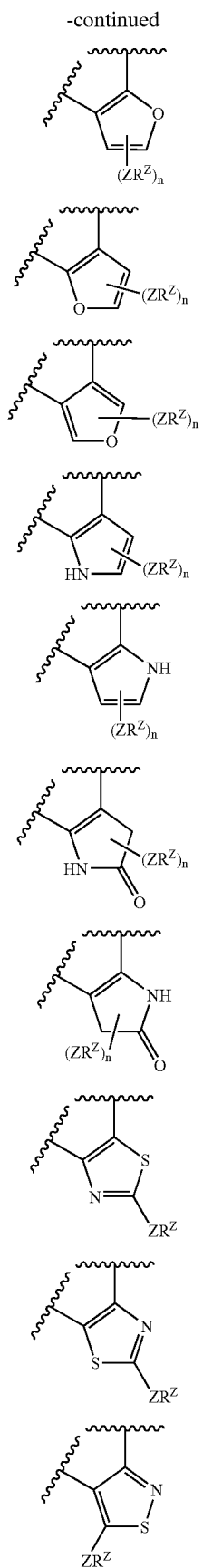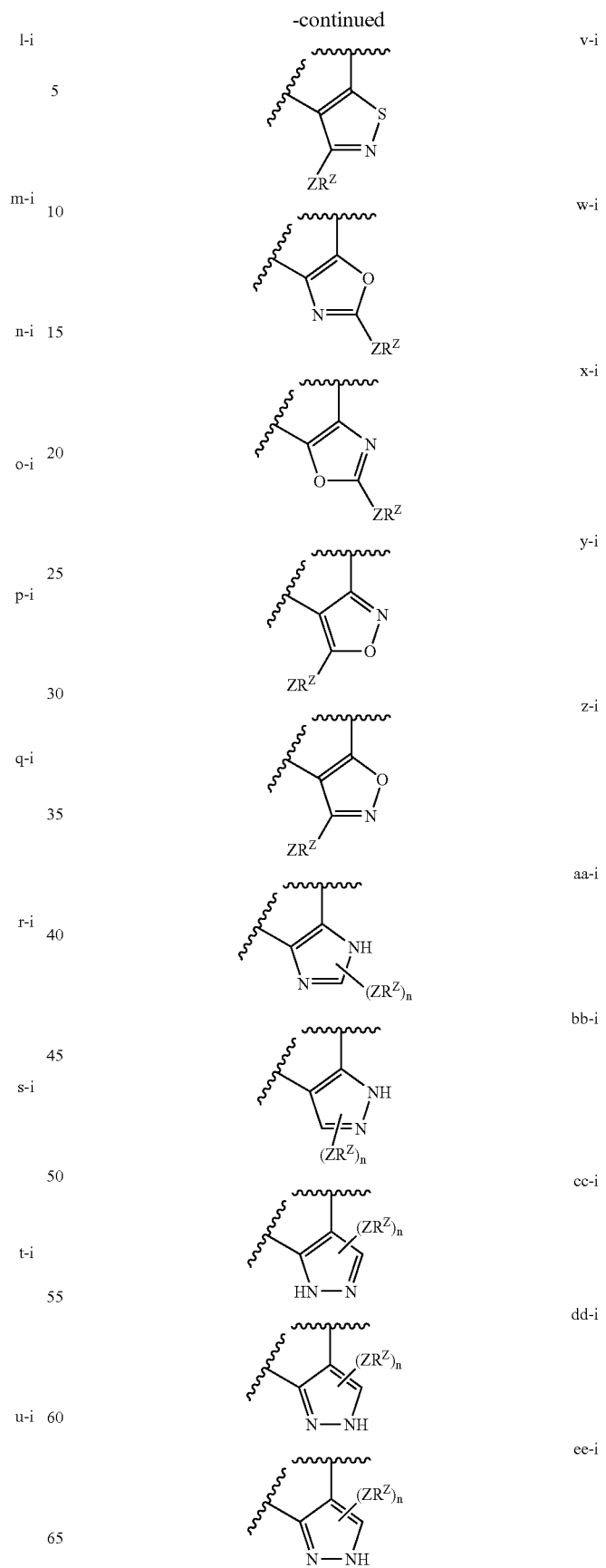

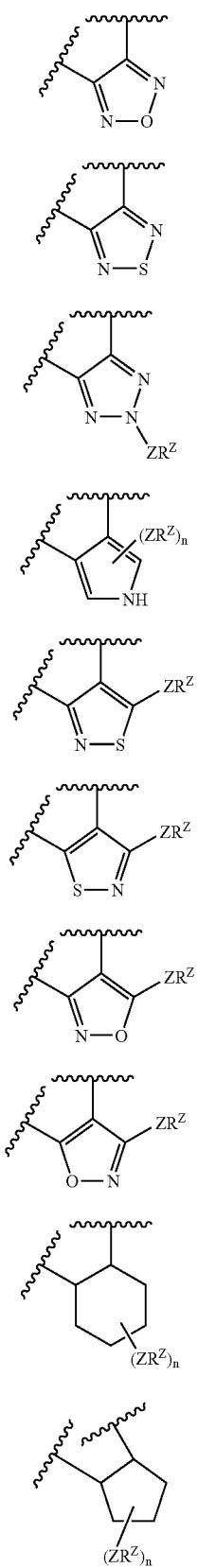
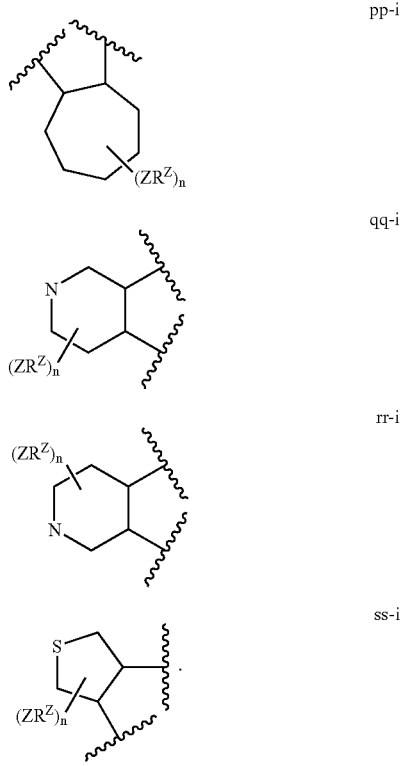

20. The compound of claim 19, wherein $R^4$ and $R^5$, taken together with the carbon atoms to which they are bound form an optionally substituted 5- or 6-membered ring selected from phenyl (a-i), pyridyl (b-i, c-i, d-i, or e-i), cyclohexyl (nn-i), or cyclopentyl (oo-i).

21. The compound of claim 20, wherein each occurrence of —$ZR^Z$, when present, is independently halogen, R', CN, $NO_2$, —N(R')$_2$, —$CH_2$N(R')$_2$, —$(CH_2)_2$N(R')$_2$, —$(CH_2)_3$N(R')$_2$, —OR', —$CH_2$OR', —$(CH_2)_2$OR', —$(CH_2)_3$OR', —SR', —$CH_2$SR', —$(CH_2)_2$SR', —$(CH_2)_3$SR', —COOR', —NRCOR', NRCOOR', —CON(R')$_2$, or —S(O)$_2$N(R')$_2$.

22. The compound of claim 20, wherein —$ZR^Z$ groups are each independently F, Cl, Br, I, —CN, —COOMe, —COOH, —OH, $NH_2$, SH, —$SO_2NH_2$, —CON(CH$_3$)$_2$, —O(C$_1$-C$_6$alkyl), —$CH_2$O(C$_1$-C$_6$alkyl), —$(CH_2)_2$O(C$_1$-C$_6$alkyl), —$(CH_2)_3$O(C$_1$-C$_6$alkyl), —S(C$_1$-C$_6$alkyl), —$CH_2$S(C$_1$-C$_6$alkyl), —$(CH_2)_2$S(C$_1$-C$_6$alkyl), —$(CH_2)_3$S(C$_1$-C$_6$alkyl), —N(C$_1$-C$_6$alkyl)$_2$, —$CH_2$N(C$_1$-C$_6$alkyl)$_2$, —$(CH_2)_2$N(C$_1$-C$_6$alkyl)$_2$, —$(CH_2)_3$N(C$_1$-C$_6$alkyl)$_2$, wherein each C$_1$-C$_6$alkyl group is optionally substituted with R', —OR', —N(R')$_2$, —SR', —SO$_2$N(R)$_2$, —NRSO$_2$R', —CON(R')$_2$, or —NRCOR', or —$ZR^Z$ groups are each independently an optionally substituted group selected from C$_1$-C$_6$alkyl, C$_3$-C$_8$cycloalkyl, phenyl, phenyloxy, benzyl, benzyloxy, pyridyl, pyrimidinyl, thienyl, N-morpholinyl, N-piperidinyl, N-piperazinyl, or furanyl.

23. The compound of any one of claim 5-8, 9-13, or 21-22, wherein G is N, X is O and $R^4$ and $R^5$, taken together form an optionally substituted phenyl group and compounds have formula V:

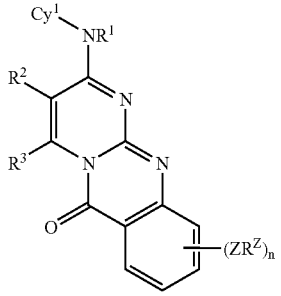

V or a pharmaceutically acceptable salt thereof.

24. The compound of claim 1, wherein G is N, X is O, and $R^4$ and $R^5$, taken together form an optionally substituted phenyl group and compounds have formula V:

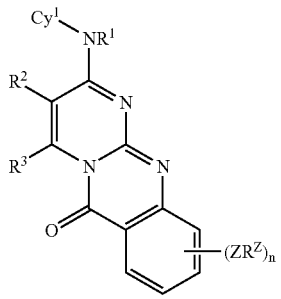

V or a pharmaceutically acceptable salt thereof.

25. The compound of claim 24, wherein $R^2$ and $R^3$, taken together with the carbon atoms to which they are bound form an optionally substituted phenyl, cyclopentyl, cyclohexyl, piperidinyl, pyrazolyl, or pyridyl group and compounds have formula V-A, V-B, V-C, V-D, V-E, or V-F:

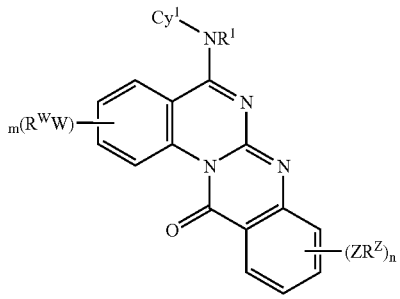

V-A

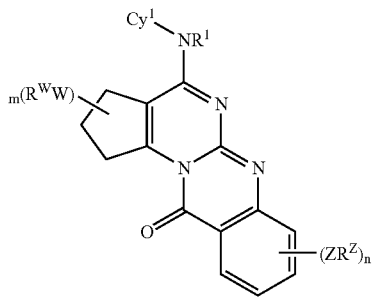

V-B

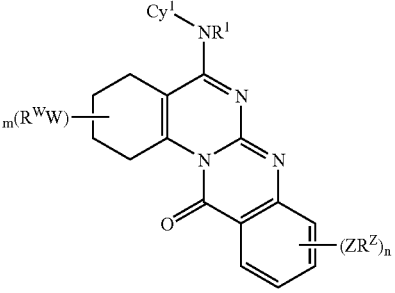

V-C

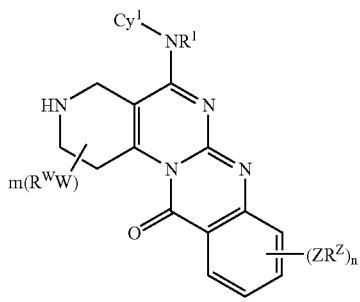

V-D

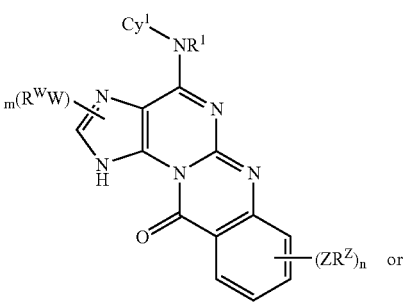

V-E or

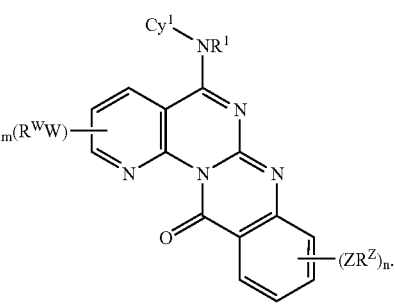

V-F

26. The compound claim 24 or claim 25, wherein
a) $R^1$ is hydrogen, —COR', CONRR', or is an optionally substituted $C_1$-$C_6$ alkyl group;
b) $Cy^1$ phenyl (i), pyridyl (iii), pyrimidinyl (iv), imidazolyl (vi), pyrazolyl (vii), triazolyl (x), thiazolyl (xiv), or indazolyl (xix) or (xxi);
c) each occurrence of —YR$^Y$, when present, is independently halogen, R', CN, $NO_2$, —N(R')$_2$, —$CH_2$N(R')$_2$, —($CH_2$)$_2$N(R')$_2$, —($CH_2$)$_3$N(R')$_2$, —OR', —$CH_2$OR', —($CH_2$)$_2$OR', —($CH_2$)$_3$OR', —SR', —$CH_2$SR', —($CH_2$)$_2$SR', —($CH_2$)$_3$SR', —COOR', —NRCOR', NRCOOR', —CON(R')$_2$, or —S(O)$_2$N(R')$_2$; and/or
d) m and n are each independently 0 or 1 and —WR$^W$ and —ZR$^Z$ groups, when present, are each independently F, Cl, Br, I, —CN, —COOMe, —COOH, —OH, $NH_2$, SH, —$SO_2NH_2$, —CON($CH_3$)$_2$, —O($C_1$-$C_6$alkyl), —$CH_2$O (C₁-C₆alkyl), —(CH₂)₂O(C₁-C₆alkyl), —(CH₂)₃O(C₁-C₆alkyl), —S(C₁-C₆alkyl), —CH₂S(C₁-C₆alkyl), —(CH₂)₂S(C₁-C₆alkyl), —(CH₂)₃S(C₁-C₆alkyl), —N(C₁-C₆alkyl)₂, —CH₂N(C₁-C₆alkyl)₂, —(CH₂)₂N(C₁-C₆alkyl)₂, —(CH₂)₃N(C₁-C₆alkyl)₂, wherein each C₁-C₆alkyl group is optionally substituted with R', —OR', —N(R')₂, —SR', —SO₂N(R')₂, —NRSO₂R', —CON(R')₂, or —NRCOR', or —WR$^W$ and —ZR$^Z$ groups are each independently an optionally substituted group selected from C₁-C₆alkyl, C₃-C₈cycloalkyl, phenyl, phenyloxy, benzyl, benzyloxy, pyridyl, pyrimidinyl, thienyl, N-morpholinyl, N-piperidinyl, N-piperazinyl, or furanyl.

27. The compound of claim 26, wherein R¹ is hydrogen.

28. The compound of claim 26, wherein Cy¹ is phenyl (i) or pyrazolyl (vii).

29. The compound of claim 28, wherein Cy¹ is pyrazolyl (vii).

30. The compound claim 29, wherein —YR$^Y$ groups are each independently F, Cl, Br, I, —CN, —COOMe, —COOH, —OH, NH₂, SH, —SO₂NH₂, —CON(CH₃)₂, —O(C₁-C₆alkyl), —CH₂O(C₁-C₆alkyl), —(CH₂)₂O(C₁-C₆alkyl), —(CH₂)₃O(C₁-C₆alkyl), —S(C₁-C₆alkyl), —CH₂S(C₁-C₆alkyl), —(CH₂)₂S(C₁-C₆alkyl), —(CH₂)₃S(C₁-C₆alkyl), —N(C₁-C₆alkyl)₂, —CH₂N(C₁-C₆alkyl)₂, —(CH₂)₂N(C₁-C₆alkyl)₂, —(CH₂)₃N(C₁-C₆alkyl)₂, wherein each C₁-C₆alkyl group is optionally substituted with R', —OR', —N(R')₂, —SR', —SO₂N(R')₂, —NRSO₂R', —CON(R')₂, or —NRCOR', or —YR$^Y$ groups are each independently an optionally substituted group selected from C₁-C₆alkyl, C₃-C₈cycloalkyl, phenyl, phenyloxy, benzyl, benzyloxy, pyridyl, pyrimidinyl, thienyl, N-morpholinyl, N-piperidinyl, N-piperazinyl, or furanyl.

31. The compound of claim 30, wherein y is 0 or 1.

32. The compound of claim 1, selected from:

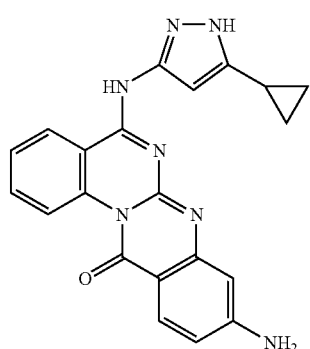

I-1

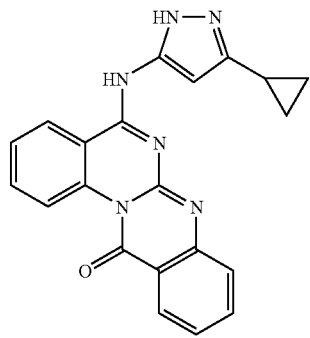

I-2

-continued

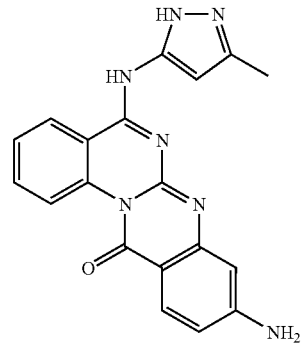

I-3

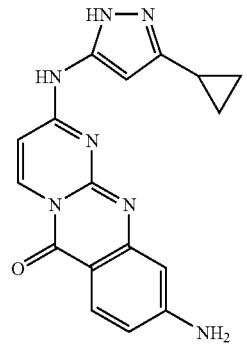

I-4

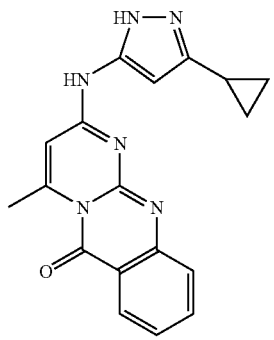

I-5

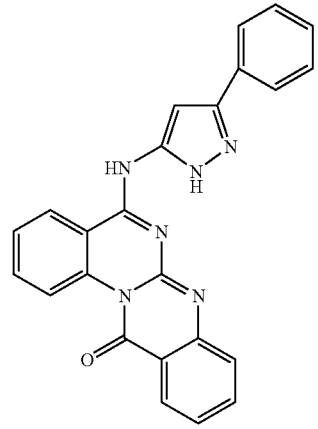

I-6

-continued
I-7
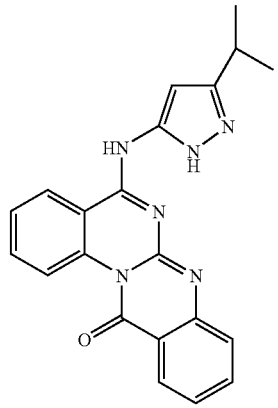
I-8
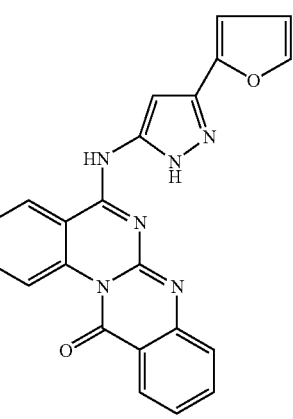
I-9
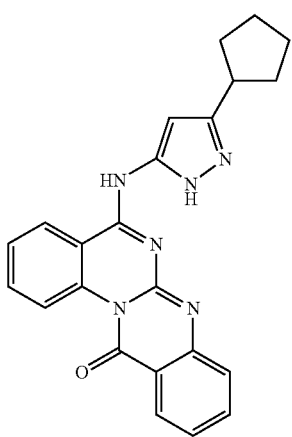
-continued
I-10
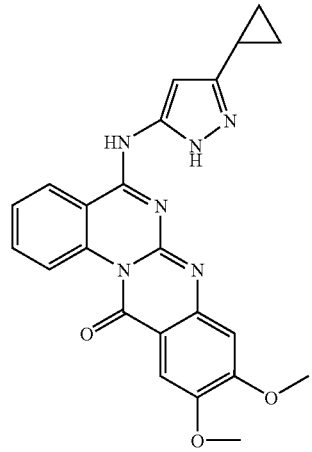
I-11
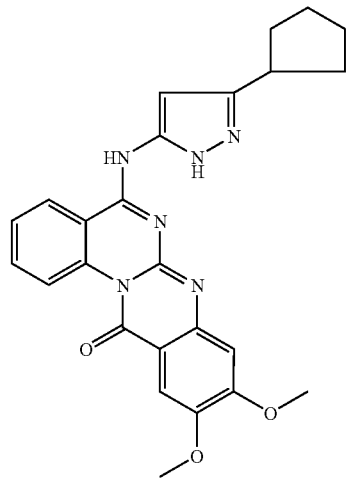
I-12
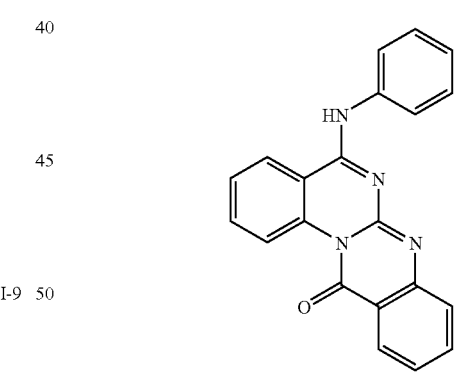
I-13
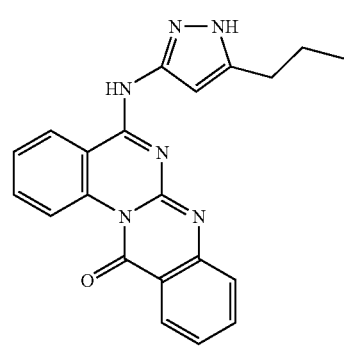

-continued
I-14
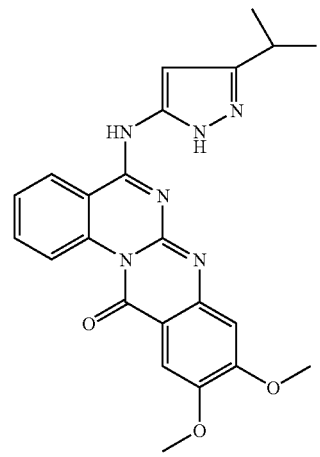
I-15
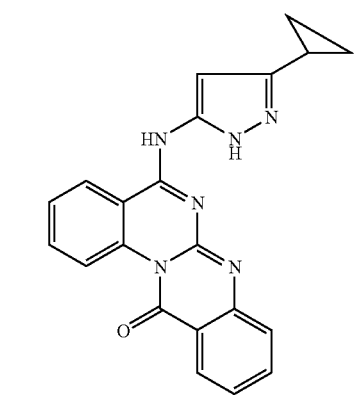
I-16
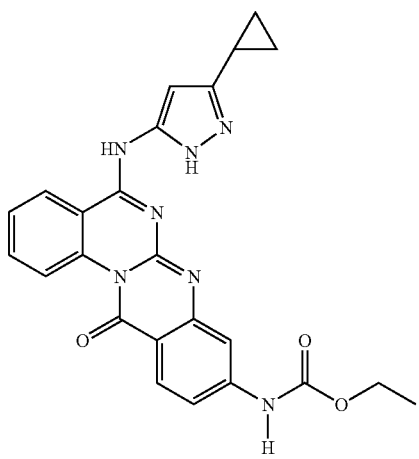
-continued
I-17
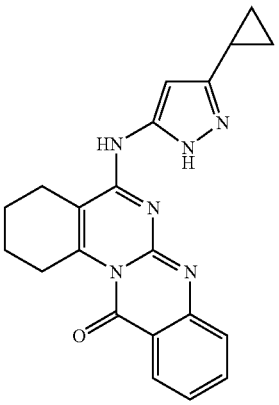
I-18
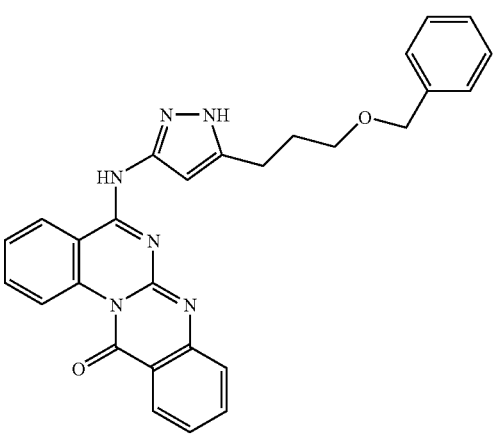
I-19
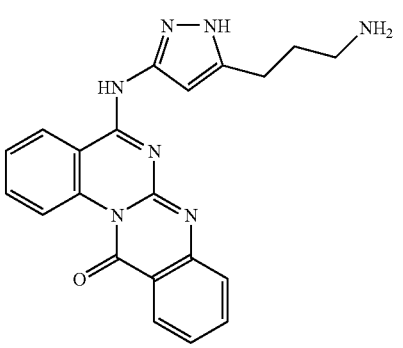
I-20
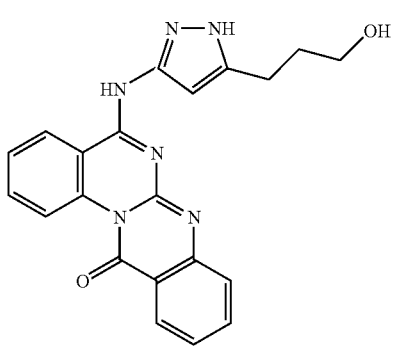

-continued

I-21
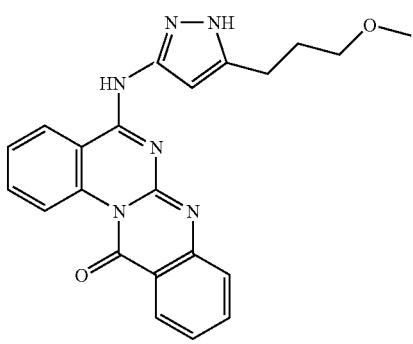

I-22
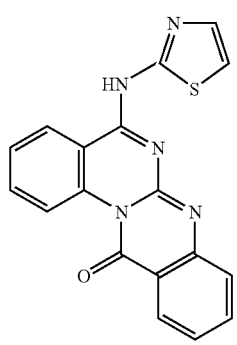

I-23
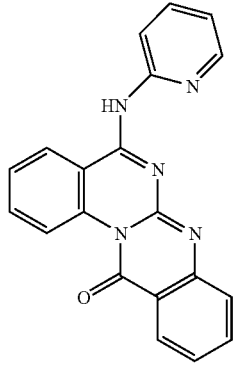

I-24
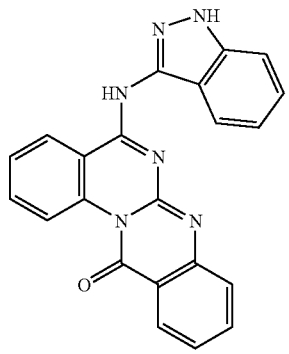

-continued

I-25
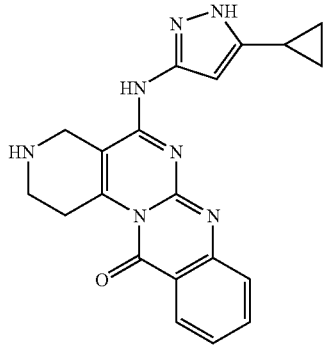

I-26
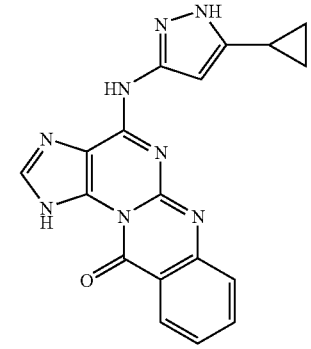

or

I-27
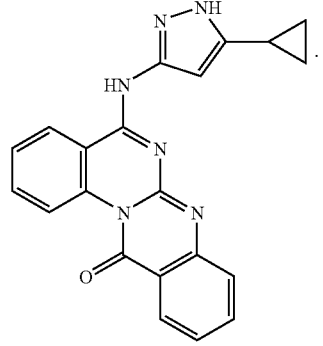

33. A composition comprising a compound of claim 1, or a pharmaceutically acceptable salt thereof, and a pharmaceutically acceptable carrier or diluent.

34. The composition of claim 33, further comprising an additional therapeutic agent selected from an agent for the treatment of an autoimmune, inflammatory, proliferative, hyperproliferative disease, or an immunologically-mediated disease including rejection of transplanted organs or tissues and Acquired Immunodeficiency Syndrome (AIDS).

35. A method of inhibiting Tec family kinase activity in a biological sample, which method comprises contacting said biological sample with the compound of claim 1.

36. A method according to claim 35, wherein the Tec family kinase is selected from Btk, Itk/Emt/Tsk, Bmx and Txk/Rlk.

* * * * *